(12) United States Patent
Spataro et al.

(10) Patent No.: US 12,357,794 B2
(45) Date of Patent: Jul. 15, 2025

(54) OPTIMIZED STRUCTURAL SUPPORT IN CATHETER INSERTION SYSTEMS

(71) Applicant: Bard Access Systems, Inc., Salt Lake City, UT (US)

(72) Inventors: Joe Spataro, Cottonwood Heights, UT (US); Austin J. Mckinnon, Herriman, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 610 days.

(21) Appl. No.: 17/558,124

(22) Filed: Dec. 21, 2021

(65) Prior Publication Data
US 2022/0193376 A1    Jun. 23, 2022

Related U.S. Application Data

(60) Provisional application No. 63/128,694, filed on Dec. 21, 2020.

(51) Int. Cl.
*A61M 25/06* (2006.01)
*A61M 25/01* (2006.01)

(52) U.S. Cl.
CPC .... *A61M 25/0606* (2013.01); *A61M 25/0113* (2013.01); *A61M 25/0693* (2013.01)

(58) Field of Classification Search
CPC .......... A61M 25/0606; A61M 25/0097; A61M 25/0693; A61M 25/09041; A61M 25/09; A61M 25/02; A61M 25/0612; A61M 2025/0175; A61M 25/0113; A61M 1/36;
(Continued)

(56) References Cited

U.S. PATENT DOCUMENTS

| 1,013,691 A | 1/1912 | Shields |
| 3,225,762 A | 12/1965 | Guttman |
| 3,325,061 A | 6/1967 | Ellsworth |

(Continued)

FOREIGN PATENT DOCUMENTS

| DE | 202012006191 U1 | 7/2012 |
| EP | 0653220 A1 | 5/1995 |

(Continued)

OTHER PUBLICATIONS

PCT/US2021/057135 filed Oct. 28, 2021 International Preliminary Report on Patentability dated May 2, 2023.

(Continued)

*Primary Examiner* — Michael J Tsai
*Assistant Examiner* — Katerina A. Wittliff
(74) *Attorney, Agent, or Firm* — Rutan & Tucker LLP

(57) ABSTRACT

Embodiments disclosed herein are directed to catheter placement systems including distally extendable support devices. When placing elongate catheters advanced insertion systems are required to maintain a "touch-free" insertion. Further longer needles are desirable to access deeper veins or penetrate deeper surface tissues. Distally extendable support devices provide columnar support to one of the elongate catheter or the needle to prevent buckling or kinking of the catheter, and maintain the needle tip within a predetermined bending arm distance. This prevents the user from contacting one of the needle or the catheter directly to provide additional support, maintaining a "touch-free" insertion.

19 Claims, 9 Drawing Sheets

(58) Field of Classification Search
CPC ... A61M 1/3621; A61M 1/3653; A61M 25/01
See application file for complete search history.

(56) References Cited

U.S. PATENT DOCUMENTS

| | | |
|---|---|---|
| 3,382,872 A | 5/1968 | Rubin |
| 3,570,485 A | 3/1971 | Reilly |
| 3,890,976 A | 6/1975 | Bazell et al. |
| 3,991,762 A | 11/1976 | Radford |
| 4,205,675 A | 6/1980 | Vaillancourt |
| 4,292,970 A | 10/1981 | Hession, Jr. |
| 4,468,224 A | 8/1984 | Enzmann et al. |
| 4,484,915 A | 11/1984 | Tartaglia |
| 4,525,157 A | 6/1985 | Vaillancourt |
| 4,581,019 A | 4/1986 | Curelaru et al. |
| 4,594,073 A | 6/1986 | Stine |
| 4,702,735 A | 10/1987 | Luther et al. |
| 4,743,265 A | 5/1988 | Whitehouse et al. |
| 4,766,908 A | 8/1988 | Clement |
| 4,863,432 A | 9/1989 | Kvalo |
| 4,935,008 A | 6/1990 | Lewis, Jr. |
| 4,950,252 A | 8/1990 | Luther et al. |
| 4,957,489 A | 9/1990 | Cameron et al. |
| 4,994,040 A | 2/1991 | Cameron et al. |
| 5,017,259 A | 5/1991 | Kohsai |
| 5,040,548 A | 8/1991 | Yock |
| 5,057,073 A | 10/1991 | Martin |
| 5,112,312 A | 5/1992 | Luther |
| 5,115,816 A | 5/1992 | Lee |
| 5,120,317 A | 6/1992 | Luther |
| 5,158,544 A | 10/1992 | Weinstein |
| 5,167,634 A | 12/1992 | Corrigan, Jr. et al. |
| 5,188,593 A | 2/1993 | Martin |
| 5,195,962 A | 3/1993 | Martin et al. |
| 5,207,650 A | 5/1993 | Martin |
| RE34,416 E | 10/1993 | Lemieux |
| 5,267,958 A | 12/1993 | Buchbinder et al. |
| 5,295,970 A | 3/1994 | Clinton et al. |
| 5,306,247 A | 4/1994 | Pfenninger |
| 5,312,361 A | 5/1994 | Zadini et al. |
| 5,322,512 A | 6/1994 | Mohiuddin |
| 5,328,472 A | 7/1994 | Steinke et al. |
| 5,350,358 A | 9/1994 | Martin |
| 5,358,495 A | 10/1994 | Lynn |
| 5,368,567 A | 11/1994 | Lee |
| 5,378,230 A | 1/1995 | Mahurkar |
| 5,380,290 A | 1/1995 | Makower et al. |
| 5,389,087 A | 2/1995 | Miraki |
| 5,439,449 A | 8/1995 | Mapes et al. |
| 5,443,457 A | 8/1995 | Ginn et al. |
| 5,460,185 A | 10/1995 | Johnson et al. |
| 5,489,271 A | 2/1996 | Andersen |
| 5,573,520 A | 11/1996 | Schwartz et al. |
| 5,683,370 A | 11/1997 | Luther et al. |
| 5,713,876 A | 2/1998 | Bogert et al. |
| 5,718,678 A | 2/1998 | Fleming, III |
| 5,772,636 A | 6/1998 | Brimhall et al. |
| 5,885,251 A | 3/1999 | Luther |
| 5,919,164 A | 7/1999 | Andersen |
| 5,921,971 A | 7/1999 | Agro et al. |
| 5,947,940 A | 9/1999 | Beisel |
| 5,951,518 A | 9/1999 | Licata et al. |
| 5,957,893 A | 9/1999 | Luther et al. |
| 5,971,957 A | 10/1999 | Luther et al. |
| 6,159,198 A | 12/2000 | Gardeski et al. |
| 6,197,007 B1 | 3/2001 | Thorne et al. |
| 6,206,849 B1 | 3/2001 | Martin et al. |
| 6,228,062 B1 | 5/2001 | Howell et al. |
| 6,475,187 B1 | 11/2002 | Gerberding |
| 6,551,284 B1 | 4/2003 | Greenberg et al. |
| 6,606,515 B1 | 8/2003 | Windheuser et al. |
| 6,616,630 B1 | 9/2003 | Woehr et al. |
| 6,626,869 B1 | 9/2003 | Bint |
| 6,638,252 B2 | 10/2003 | Moulton et al. |
| 6,716,228 B2 | 4/2004 | Tal |
| 6,726,659 B1 | 4/2004 | Stocking et al. |
| 6,819,951 B2 | 11/2004 | Patel et al. |
| 6,821,287 B1 | 11/2004 | Jang |
| 6,926,692 B2 | 8/2005 | Katoh et al. |
| 6,962,575 B2 | 11/2005 | Tal |
| 6,991,625 B1 | 1/2006 | Gately et al. |
| 6,994,693 B2 | 2/2006 | Tal |
| 6,999,809 B2 | 2/2006 | Currier et al. |
| 7,025,746 B2 | 4/2006 | Tal |
| 7,029,467 B2 | 4/2006 | Currier et al. |
| 7,037,293 B2 | 5/2006 | Carrillo et al. |
| 7,074,231 B2 | 7/2006 | Jang |
| 7,094,222 B1 | 8/2006 | Siekas et al. |
| 7,141,050 B2 | 11/2006 | Deal et al. |
| 7,144,386 B2 | 12/2006 | Korkor et al. |
| 7,311,697 B2 | 12/2007 | Osborne |
| 7,364,566 B2 | 4/2008 | Elkins et al. |
| 7,377,910 B2 | 5/2008 | Katoh et al. |
| 7,390,323 B2 | 6/2008 | Jang |
| D600,793 S | 9/2009 | Bierman et al. |
| D601,242 S | 9/2009 | Bierman et al. |
| D601,243 S | 9/2009 | Bierman et al. |
| 7,594,911 B2 | 9/2009 | Powers et al. |
| 7,691,093 B2 | 4/2010 | Brimhall |
| 7,722,567 B2 | 5/2010 | Tal |
| D617,893 S | 6/2010 | Bierman et al. |
| D624,643 S | 9/2010 | Bierman et al. |
| 7,819,889 B2 | 10/2010 | Healy et al. |
| 7,857,788 B2 | 12/2010 | Racz |
| D630,729 S | 1/2011 | Bierman et al. |
| 7,909,797 B2 | 3/2011 | Kennedy, II et al. |
| 7,909,811 B2 | 3/2011 | Agro et al. |
| 7,922,696 B2 | 4/2011 | Tal et al. |
| 7,938,820 B2 | 5/2011 | Webster et al. |
| 7,967,834 B2 | 6/2011 | Tal et al. |
| 7,976,511 B2 | 7/2011 | Fojtik |
| 7,985,204 B2 | 7/2011 | Katoh et al. |
| 8,073,517 B1 | 12/2011 | Burchman |
| 8,105,286 B2 | 1/2012 | Anderson et al. |
| 8,192,402 B2 | 6/2012 | Anderson et al. |
| 8,202,251 B2 | 6/2012 | Bierman et al. |
| 8,206,356 B2 | 6/2012 | Katoh et al. |
| 8,361,011 B2 | 1/2013 | Mendels |
| 8,372,107 B2 | 2/2013 | Tupper |
| 8,377,006 B2 | 2/2013 | Tal et al. |
| 8,454,577 B2 | 6/2013 | Joergensen et al. |
| 8,585,858 B2 | 11/2013 | Kronfeld et al. |
| 8,657,790 B2 | 2/2014 | Tal et al. |
| 8,672,888 B2 | 3/2014 | Tal |
| 8,696,645 B2 | 4/2014 | Tal et al. |
| 8,784,362 B2 | 7/2014 | Boutilette et al. |
| 8,827,958 B2 | 9/2014 | Bierman et al. |
| 8,876,704 B2 | 11/2014 | Golden et al. |
| 8,882,713 B1 | 11/2014 | Call et al. |
| 8,900,192 B2 | 12/2014 | Anderson et al. |
| 8,900,207 B2 | 12/2014 | Uretsky |
| 8,915,884 B2 | 12/2014 | Tal et al. |
| 8,956,327 B2 | 2/2015 | Bierman et al. |
| 9,023,093 B2 | 5/2015 | Pal |
| 9,067,023 B2 | 6/2015 | Bertocci |
| 9,126,012 B2 | 9/2015 | McKinnon et al. |
| 9,138,252 B2 | 9/2015 | Bierman et al. |
| 9,180,275 B2 | 11/2015 | Helm |
| 9,265,920 B2 | 2/2016 | Rundquist et al. |
| 9,272,121 B2 | 3/2016 | Piccagli |
| 9,445,734 B2 | 9/2016 | Grunwald |
| 9,522,254 B2 | 12/2016 | Belson |
| 9,554,785 B2 | 1/2017 | Walters et al. |
| 9,566,087 B2 | 2/2017 | Bierman et al. |
| 9,675,784 B2 | 6/2017 | Belson |
| 9,713,695 B2 | 7/2017 | Bunch et al. |
| 9,764,117 B2 | 9/2017 | Bierman et al. |
| 9,770,573 B2 | 9/2017 | Golden et al. |
| 9,814,861 B2 | 11/2017 | Boutillette et al. |
| 9,820,845 B2 | 11/2017 | von Lehe et al. |
| 9,861,383 B2 | 1/2018 | Clark |
| 9,872,971 B2 | 1/2018 | Blanchard |
| 9,884,169 B2 | 2/2018 | Bierman et al. |
| 9,889,275 B2 | 2/2018 | Voss et al. |

(56) References Cited

U.S. PATENT DOCUMENTS

| | | |
|---|---|---|
| 9,913,585 B2 | 3/2018 | McCaffrey et al. |
| 9,913,962 B2 | 3/2018 | Tal et al. |
| 9,981,113 B2 | 5/2018 | Bierman |
| 10,010,312 B2 | 7/2018 | Tegels |
| 10,065,020 B2 | 9/2018 | Gaur |
| 10,086,170 B2 | 10/2018 | Chhikara et al. |
| 10,098,724 B2 | 10/2018 | Adams et al. |
| 10,111,683 B2 | 10/2018 | Tsamir et al. |
| 10,118,020 B2 | 11/2018 | Avneri et al. |
| 10,130,269 B2 | 11/2018 | McCaffrey et al. |
| 10,220,184 B2 | 3/2019 | Clark |
| 10,220,191 B2 | 3/2019 | Belson et al. |
| 10,265,508 B2 | 4/2019 | Baid |
| 10,271,873 B2 | 4/2019 | Steingisser et al. |
| 10,376,675 B2 | 8/2019 | Mitchell et al. |
| 10,675,440 B2 | 6/2020 | Abitabilo et al. |
| 10,688,281 B2 * | 6/2020 | Blanchard ......... A61M 25/0105 |
| 10,806,901 B2 | 10/2020 | Burkholz et al. |
| 10,926,060 B2 | 2/2021 | Stern et al. |
| 11,260,206 B2 | 3/2022 | Stone et al. |
| 11,400,260 B2 * | 8/2022 | Huang ................. A61M 25/01 |
| 11,759,607 B1 | 9/2023 | Biancarelli |
| 2002/0040231 A1 | 4/2002 | Wysoki |
| 2002/0045843 A1 | 4/2002 | Barker et al. |
| 2002/0198492 A1 | 12/2002 | Miller et al. |
| 2003/0036712 A1 | 2/2003 | Heh et al. |
| 2003/0060863 A1 | 3/2003 | Dobak |
| 2003/0088212 A1 | 5/2003 | Tal |
| 2003/0100849 A1 | 5/2003 | Jang |
| 2003/0153874 A1 | 8/2003 | Tal |
| 2003/0158514 A1 | 8/2003 | Tal |
| 2004/0015138 A1 | 1/2004 | Currier et al. |
| 2004/0064086 A1 | 4/2004 | Gottlieb et al. |
| 2004/0116864 A1 | 6/2004 | Boudreaux |
| 2004/0116901 A1 | 6/2004 | Appling |
| 2004/0167478 A1 | 8/2004 | Mooney et al. |
| 2004/0193093 A1 | 9/2004 | Desmond |
| 2004/0230178 A1 | 11/2004 | Wu |
| 2005/0004554 A1 | 1/2005 | Osborne |
| 2005/0120523 A1 | 6/2005 | Schweikert |
| 2005/0131343 A1 | 6/2005 | Abrams et al. |
| 2005/0215956 A1 | 9/2005 | Nerney |
| 2005/0215958 A1 | 9/2005 | Hawthorne |
| 2005/0245882 A1 | 11/2005 | Elkins et al. |
| 2005/0283221 A1 | 12/2005 | Mann et al. |
| 2006/0009740 A1 | 1/2006 | Higgins et al. |
| 2006/0116629 A1 | 6/2006 | Tal et al. |
| 2006/0129100 A1 | 6/2006 | Tal |
| 2006/0129130 A1 | 6/2006 | Tal et al. |
| 2007/0276288 A1 | 11/2007 | Khaw |
| 2008/0045894 A1 | 2/2008 | Perchik et al. |
| 2008/0125744 A1 | 5/2008 | Treacy |
| 2008/0125748 A1 | 5/2008 | Patel |
| 2008/0132850 A1 | 6/2008 | Fumiyama et al. |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0312578 A1 | 12/2008 | DeFonzo et al. |
| 2008/0319387 A1 | 12/2008 | Amisar et al. |
| 2009/0187147 A1 | 7/2009 | Kurth et al. |
| 2009/0221961 A1 | 9/2009 | Tal et al. |
| 2009/0270889 A1 | 10/2009 | Tal et al. |
| 2009/0292272 A1 | 11/2009 | McKinnon |
| 2010/0030154 A1 | 2/2010 | Duffy |
| 2010/0256487 A1 | 10/2010 | Hawkins et al. |
| 2010/0298839 A1 | 11/2010 | Castro |
| 2010/0305474 A1 | 12/2010 | DeMars et al. |
| 2011/0004162 A1 | 1/2011 | Tal |
| 2011/0009827 A1 | 1/2011 | Bierman et al. |
| 2011/0021994 A1 | 1/2011 | Anderson et al. |
| 2011/0066142 A1 | 3/2011 | Tal et al. |
| 2011/0071502 A1 | 3/2011 | Asai |
| 2011/0144620 A1 | 6/2011 | Tal |
| 2011/0152836 A1 | 6/2011 | Riopelle et al. |
| 2011/0190778 A1 | 8/2011 | Arpasi et al. |
| 2011/0202006 A1 | 8/2011 | Bierman et al. |
| 2011/0251559 A1 | 10/2011 | Tal et al. |
| 2011/0270192 A1 | 11/2011 | Anderson et al. |
| 2012/0041371 A1 | 2/2012 | Tal et al. |
| 2012/0065590 A1 | 3/2012 | Bierman et al. |
| 2012/0078231 A1 | 3/2012 | Hoshinouchi |
| 2012/0130411 A1 | 5/2012 | Tal et al. |
| 2012/0130415 A1 | 5/2012 | Tal et al. |
| 2012/0157854 A1 | 6/2012 | Kurrus et al. |
| 2012/0215171 A1 | 8/2012 | Christiansen |
| 2012/0220942 A1 | 8/2012 | Hall et al. |
| 2012/0226239 A1 | 9/2012 | Green |
| 2012/0283640 A1 | 11/2012 | Anderson et al. |
| 2012/0316500 A1 | 12/2012 | Bierman et al. |
| 2013/0053763 A1 | 2/2013 | Makino et al. |
| 2013/0053826 A1 | 2/2013 | Shevgoor |
| 2013/0123704 A1 | 5/2013 | Bierman et al. |
| 2013/0158338 A1 | 6/2013 | Kelly et al. |
| 2013/0188291 A1 | 7/2013 | Vardiman |
| 2013/0237931 A1 | 9/2013 | Tal et al. |
| 2013/0306079 A1 | 11/2013 | Tracy |
| 2014/0025036 A1 | 1/2014 | Bierman et al. |
| 2014/0081210 A1 | 3/2014 | Bierman et al. |
| 2014/0094774 A1 | 4/2014 | Blanchard |
| 2014/0100552 A1 | 4/2014 | Gallacher et al. |
| 2014/0207052 A1 | 7/2014 | Tal et al. |
| 2014/0207069 A1 | 7/2014 | Bierman et al. |
| 2014/0214005 A1 | 7/2014 | Belson |
| 2014/0257111 A1 | 9/2014 | Yamashita et al. |
| 2014/0276432 A1 | 9/2014 | Bierman et al. |
| 2014/0276599 A1 | 9/2014 | Cully et al. |
| 2015/0011834 A1 | 1/2015 | Ayala et al. |
| 2015/0080939 A1 | 3/2015 | Adams et al. |
| 2015/0094653 A1 | 4/2015 | Pacheco et al. |
| 2015/0112307 A1 | 4/2015 | Margolis |
| 2015/0112310 A1 | 4/2015 | Call et al. |
| 2015/0126930 A1 | 5/2015 | Bierman et al. |
| 2015/0148595 A1 | 5/2015 | Bagwell et al. |
| 2015/0190168 A1 | 7/2015 | Bierman et al. |
| 2015/0196210 A1 | 7/2015 | McCaffrey et al. |
| 2015/0224287 A1 | 8/2015 | Bian et al. |
| 2015/0231364 A1 | 8/2015 | Blanchard et al. |
| 2015/0283357 A1 | 10/2015 | Lampropoulos et al. |
| 2015/0297868 A1 | 10/2015 | Tal et al. |
| 2015/0320969 A1 | 11/2015 | Haslinger et al. |
| 2015/0320977 A1 | 11/2015 | Vitullo et al. |
| 2015/0351793 A1 | 12/2015 | Bierman et al. |
| 2015/0359549 A1 | 12/2015 | Lenker et al. |
| 2015/0359998 A1 | 12/2015 | Carmel et al. |
| 2016/0082223 A1 | 3/2016 | Barnell |
| 2016/0114124 A1 | 4/2016 | Tal |
| 2016/0158523 A1 | 6/2016 | Helm |
| 2016/0220786 A1 | 8/2016 | Mitchell et al. |
| 2016/0242661 A1 | 8/2016 | Fischell et al. |
| 2016/0256101 A1 | 9/2016 | Aharoni et al. |
| 2016/0325073 A1 | 11/2016 | Davies et al. |
| 2016/0333198 A1 * | 11/2016 | Blanchard ......... A61M 25/0618 |
| 2016/0338728 A1 | 11/2016 | Tal |
| 2016/0346503 A1 | 12/2016 | Jackson et al. |
| 2017/0028135 A1 | 2/2017 | Fransson et al. |
| 2017/0035990 A1 | 2/2017 | Swift |
| 2017/0072165 A1 | 3/2017 | Lim et al. |
| 2017/0120000 A1 | 5/2017 | Osypka et al. |
| 2017/0120014 A1 | 5/2017 | Harding et al. |
| 2017/0120034 A1 | 5/2017 | Kaczorowski |
| 2017/0128700 A1 | 5/2017 | Roche Rebollo |
| 2017/0156987 A1 | 6/2017 | Babbs et al. |
| 2017/0172653 A1 | 6/2017 | Urbanski et al. |
| 2017/0182293 A1 | 6/2017 | Chhikara et al. |
| 2017/0239443 A1 | 8/2017 | Abitabilo et al. |
| 2017/0259043 A1 | 9/2017 | Chan et al. |
| 2017/0273713 A1 | 9/2017 | Shah et al. |
| 2017/0296792 A1 | 10/2017 | Ornelas Vargas et al. |
| 2017/0326339 A1 | 11/2017 | Bailey et al. |
| 2017/0361070 A1 | 12/2017 | Hivert |
| 2017/0368255 A1 | 12/2017 | Provost et al. |
| 2018/0001062 A1 | 1/2018 | O'Carrol et al. |
| 2018/0008294 A1 | 1/2018 | Garrison et al. |
| 2018/0021545 A1 | 1/2018 | Mitchell et al. |

(56) References Cited

U.S. PATENT DOCUMENTS

| | | |
|---|---|---|
| 2018/0116690 A1 | 5/2018 | Sarabia et al. |
| 2018/0117284 A1 | 5/2018 | Appling et al. |
| 2018/0133438 A1 | 5/2018 | Hulvershorn et al. |
| 2018/0154062 A1 | 6/2018 | DeFonzo et al. |
| 2018/0154112 A1 | 6/2018 | Chan et al. |
| 2018/0214674 A1 | 8/2018 | Ebnet et al. |
| 2018/0296799 A1 | 10/2018 | Horst et al. |
| 2018/0296804 A1 | 10/2018 | Bierman |
| 2018/0310955 A1 | 11/2018 | Lindekugel et al. |
| 2019/0015646 A1 | 1/2019 | Matlock et al. |
| 2019/0021640 A1 | 1/2019 | Burkholz et al. |
| 2019/0060616 A1 | 2/2019 | Solomon |
| 2019/0076167 A1 | 3/2019 | Fantuzzi et al. |
| 2019/0134349 A1 | 5/2019 | Cohn et al. |
| 2019/0192824 A1 | 6/2019 | Cordeiro et al. |
| 2019/0201665 A1 | 7/2019 | Turpin |
| 2019/0209812 A1 | 7/2019 | Burkholz et al. |
| 2019/0255294 A1 | 8/2019 | Mitchell et al. |
| 2019/0255298 A1 | 8/2019 | Mitchell et al. |
| 2019/0275303 A1 | 9/2019 | Tran et al. |
| 2019/0276268 A1 | 9/2019 | Akingba |
| 2019/0321590 A1 | 10/2019 | Burkholz et al. |
| 2019/0351196 A1* | 11/2019 | Ribelin ............ A61M 25/09041 |
| 2020/0001051 A1 | 1/2020 | Huang et al. |
| 2020/0016374 A1 | 1/2020 | Burkholz et al. |
| 2020/0046948 A1 | 2/2020 | Burkholz et al. |
| 2020/0100716 A1 | 4/2020 | Devgon et al. |
| 2020/0129732 A1 | 4/2020 | Vogt et al. |
| 2020/0147349 A1 | 5/2020 | Holt |
| 2020/0197682 A1 | 6/2020 | Franklin et al. |
| 2020/0197684 A1 | 6/2020 | Wax |
| 2020/0237278 A1 | 7/2020 | Asbaghi |
| 2020/0359995 A1 | 11/2020 | Walsh et al. |
| 2021/0030944 A1 | 2/2021 | Cushen et al. |
| 2021/0060306 A1 | 3/2021 | Kumar |
| 2021/0069471 A1 | 3/2021 | Howell |
| 2021/0085927 A1 | 3/2021 | Howell |
| 2021/0100985 A1 | 4/2021 | Akcay et al. |
| 2021/0113809 A1 | 4/2021 | Howell |
| 2021/0113810 A1 | 4/2021 | Howell |
| 2021/0113816 A1 | 4/2021 | DiCianni |
| 2021/0121661 A1 | 4/2021 | Howell |
| 2021/0121667 A1 | 4/2021 | Howell |
| 2021/0228842 A1 | 7/2021 | Scherich et al. |
| 2021/0228843 A1 | 7/2021 | Howell et al. |
| 2021/0244920 A1 | 8/2021 | Kujawa et al. |
| 2021/0290898 A1 | 9/2021 | Burkholz |
| 2021/0290901 A1 | 9/2021 | Burkholz et al. |
| 2021/0290913 A1 | 9/2021 | Horst et al. |
| 2021/0322729 A1 | 10/2021 | Howell |
| 2021/0330941 A1 | 10/2021 | Howell et al. |
| 2021/0330942 A1 | 10/2021 | Howell |
| 2021/0361915 A1 | 11/2021 | Howell et al. |
| 2021/0402149 A1 | 12/2021 | Howell |
| 2021/0402153 A1 | 12/2021 | Howell et al. |
| 2022/0001109 A1 | 1/2022 | Simon |
| 2022/0001138 A1 | 1/2022 | Howell |
| 2022/0032013 A1 | 2/2022 | Howell et al. |
| 2022/0032014 A1 | 2/2022 | Howell et al. |
| 2022/0062528 A1 | 3/2022 | Thornley et al. |
| 2022/0062596 A1* | 3/2022 | Ribelin ............ A61M 25/0105 |
| 2022/0126064 A1 | 4/2022 | Tobin et al. |
| 2022/0193377 A1 | 6/2022 | Haymond et al. |
| 2022/0193378 A1 | 6/2022 | Spataro et al. |
| 2022/0323723 A1 | 10/2022 | Spataro et al. |
| 2022/0331562 A1* | 10/2022 | Jaros ............ A61M 25/0097 |
| 2022/0331563 A1 | 10/2022 | Papadia |
| 2023/0042898 A1 | 2/2023 | Howell et al. |
| 2023/0096377 A1 | 3/2023 | West et al. |
| 2023/0096740 A1 | 3/2023 | Bechstein et al. |
| 2023/0099654 A1 | 3/2023 | Blanchard et al. |
| 2023/0100482 A1 | 3/2023 | Howell |
| 2023/0101455 A1 | 3/2023 | Howell et al. |
| 2023/0102231 A1 | 3/2023 | Bechstein et al. |
| 2023/0173231 A1* | 6/2023 | Parikh ............ A61M 25/0113 604/510 |
| 2023/0233814 A1 | 7/2023 | Howell et al. |
| 2023/0381459 A1* | 11/2023 | Belson ............ A61M 25/0041 |
| 2024/0009427 A1 | 1/2024 | Howell et al. |
| 2024/0050706 A1 | 2/2024 | Howell et al. |
| 2024/0198058 A1 | 6/2024 | Howell et al. |
| 2025/0001136 A1 | 1/2025 | Mitchell et al. |
| 2025/0065083 A1 | 2/2025 | Haymond et al. |
| 2025/0082906 A1 | 3/2025 | Howell et al. |

FOREIGN PATENT DOCUMENTS

| | | |
|---|---|---|
| EP | 0730880 A1 | 9/1996 |
| EP | 2061385 A1 | 5/2009 |
| EP | 1458437 B1 | 3/2010 |
| EP | 2248549 A2 | 11/2010 |
| EP | 2319576 A1 | 5/2011 |
| EP | 2366422 A1 | 9/2011 |
| EP | 2486880 A2 | 8/2012 |
| EP | 2486881 A2 | 8/2012 |
| EP | 2486951 A2 | 8/2012 |
| EP | 2512576 A2 | 10/2012 |
| EP | 2152348 B1 | 2/2015 |
| EP | 3473291 A1 | 4/2019 |
| EP | 3093038 B1 | 5/2019 |
| EP | 2260897 B1 | 9/2019 |
| EP | 3693051 A1 | 8/2020 |
| GB | 1273547 A | 5/1972 |
| JP | 2004248987 A | 9/2004 |
| JP | 2008054859 A | 3/2008 |
| WO | 94/21315 A1 | 9/1994 |
| WO | 95/32009 A2 | 11/1995 |
| WO | 98/44979 A1 | 10/1998 |
| WO | 98/53871 A1 | 12/1998 |
| WO | WO-9857685 A1 * | 12/1998 ........ A61M 25/0693 |
| WO | 99/12600 A1 | 3/1999 |
| WO | 99/26681 A1 | 6/1999 |
| WO | 00/06221 A1 | 2/2000 |
| WO | 0054830 A1 | 9/2000 |
| WO | 2003008020 A1 | 1/2003 |
| WO | 2003057272 A2 | 7/2003 |
| WO | 03/068073 A1 | 8/2003 |
| WO | 2003066125 A2 | 8/2003 |
| WO | 2005096778 A2 | 10/2005 |
| WO | 2006055288 A2 | 5/2006 |
| WO | 2006055780 A2 | 5/2006 |
| WO | 2007046850 A2 | 4/2007 |
| WO | 2008033983 A1 | 3/2008 |
| WO | 2008092029 A2 | 7/2008 |
| WO | 2008/131300 A2 | 10/2008 |
| WO | 2008131289 A2 | 10/2008 |
| WO | 2009114833 A1 | 9/2009 |
| WO | 2009114837 A2 | 9/2009 |
| WO | 2010/048449 A2 | 4/2010 |
| WO | 2010056906 A2 | 5/2010 |
| WO | 2010083467 A2 | 7/2010 |
| WO | 2010/132608 A2 | 11/2010 |
| WO | 2011081859 A2 | 7/2011 |
| WO | 2011097639 A2 | 8/2011 |
| WO | 2011109792 A1 | 9/2011 |
| WO | 2011146764 A1 | 11/2011 |
| WO | 2012068162 A2 | 5/2012 |
| WO | 2012068166 A2 | 5/2012 |
| WO | 2012135761 A1 | 10/2012 |
| WO | 2012/154277 A1 | 11/2012 |
| WO | 2012162677 A1 | 11/2012 |
| WO | 2013026045 A1 | 2/2013 |
| WO | 2013138519 A1 | 9/2013 |
| WO | 2014006403 A1 | 1/2014 |
| WO | 2014/100392 A1 | 6/2014 |
| WO | 2014113257 A2 | 7/2014 |
| WO | 2014152005 A2 | 9/2014 |
| WO | 2014197614 A2 | 12/2014 |
| WO | 2015057766 A1 | 4/2015 |
| WO | 2015077560 A1 | 5/2015 |
| WO | 2015/168655 A2 | 11/2015 |
| WO | 2016110824 A1 | 7/2016 |
| WO | 2016123278 A1 | 8/2016 |

(56) References Cited

FOREIGN PATENT DOCUMENTS

| | | | |
|---|---|---|---|
| WO | 2016139590 A1 | 9/2016 | |
| WO | 2016139597 A2 | 9/2016 | |
| WO | 2016/178974 A1 | 11/2016 | |
| WO | 2016/187063 A1 | 11/2016 | |
| WO | 2016176065 A1 | 11/2016 | |
| WO | 2018089275 A1 | 5/2018 | |
| WO | 2018089285 A1 | 5/2018 | |
| WO | 2018089385 A1 | 5/2018 | |
| WO | 2018191547 A1 | 10/2018 | |
| WO | 2018213148 A1 | 11/2018 | |
| WO | 2018218236 A1 | 11/2018 | |
| WO | 2019/050576 A1 | 3/2019 | |
| WO | 2019/146026 A1 | 8/2019 | |
| WO | 2019199734 A1 | 10/2019 | |
| WO | 2020014149 A1 | 1/2020 | |
| WO | 2020069395 A1 | 4/2020 | |
| WO | 2020/109448 A1 | 6/2020 | |
| WO | 2020/113123 A1 | 6/2020 | |
| WO | 2021050302 A1 | 3/2021 | |
| WO | WO-2021038041 A1 * | 3/2021 | ........ A61M 25/0009 |
| WO | 2021/077103 A1 | 4/2021 | |
| WO | 2021062023 A1 | 4/2021 | |
| WO | 2021081205 A1 | 4/2021 | |
| WO | 2021086793 A1 | 5/2021 | |
| WO | 2021/236950 A1 | 11/2021 | |
| WO | WO-2021226050 A1 * | 11/2021 | ........ A61M 25/0113 |
| WO | 2022/031618 A1 | 2/2022 | |
| WO | 2022/094141 A1 | 5/2022 | |
| WO | 2022/133297 A1 | 6/2022 | |
| WO | 2022-140406 A1 | 6/2022 | |
| WO | 2022/140429 A1 | 6/2022 | |
| WO | 2022/217098 A1 | 10/2022 | |
| WO | 2023014994 A1 | 2/2023 | |
| WO | 2023049498 A1 | 3/2023 | |
| WO | 2023049505 A1 | 3/2023 | |
| WO | 2023049511 A1 | 3/2023 | |
| WO | 2023049519 A1 | 3/2023 | |
| WO | 2023049522 A1 | 3/2023 | |
| WO | 2023146792 A1 | 8/2023 | |

OTHER PUBLICATIONS

PCT/US2021/057135 filed Oct. 28, 2021 International Search Report and Written Opinion dated Mar. 11, 2022.

PCT/US2023/011173 filed Jan. 19, 2023 International Search Report and Written Opinion dated May 22, 2023.

U.S. Appl. No. 17/240,591, filed Apr. 26, 2021 Non-Final Office Action dated Jun. 8, 2023.

U.S. Appl. No. 17/326,017, filed May 20, 2021 Notice of Allowance dated Jul. 3, 2023.

U.S. Appl. No. 17/358,504, filed Jun. 25, 2021 Restriction Requirement dated Jun. 7, 2023.

U.S. Appl. No. 17/360,694, filed Jun. 28, 2021 Restriction Requirement dated Jul. 20, 2023.

U.S. Appl. No. 17/392,061, filed Aug. 2, 2021 Non-Final Office Action dated Jul. 17, 2023.

U.S. Appl. No. 17/156,252, filed Jan. 22, 2021 Notice of Allowance dated Aug. 9, 2023.

U.S. Appl. No. 17/237,909, filed Apr. 22, 2021 Non-Final Office Action dated Jul. 27, 2023.

U.S. Appl. No. 17/358,504, filed Jun. 25, 2021 Non-Final Office Action dated Oct. 4, 2023.

U.S. Appl. No. 17/360,694, filed Jun. 28, 2021 Non-Final Office Action dated Oct. 13, 2023.

U.S. Appl. No. 17/390,682, filed Jul. 30, 2021 Final Office Action dated Jul. 27, 2023.

U.S. Appl. No. 17/513,789, filed Oct. 28, 2021 Restriction Requirement dated Oct. 3, 2023.

U.S. Appl. No. 16/398,020, filed Apr. 29, 2019 Board Decision dated Oct. 30, 2023.

U.S. Appl. No. 16/398,020, filed Apr. 29, 2019 Non-Final Office Action dated Jan. 18, 2024.

U.S. Appl. No. 17/234,611, filed Apr. 19, 2021 Restriction Requirement dated Jan. 18, 2024.

U.S. Appl. No. 17/237,909, filed Apr. 22, 2021 Notice of Allowance dated Oct. 27, 2023.

U.S. Appl. No. 17/240,591, filed Apr. 26, 2021 Final Office Action dated Dec. 6, 2023.

U.S. Appl. No. 17/390,682, filed Jul. 30, 2021 Non-Final Office Action dated Dec. 1, 2023.

U.S. Appl. No. 17/392,061, filed Aug. 2, 2021 Final Office Action dated Nov. 21, 2023.

U.S. Appl. No. 17/513,789, filed Oct. 28, 2021 Non-Final Office Action dated Jan. 9, 2024.

U.S. Appl. No. 17/557,924, filed Dec. 21, 2021 Non-Final Office Action dated Nov. 3, 2023.

PCT/US2021/028018 filed Apr. 19, 2021 International Preliminary Report on Patentability dated Jun. 3, 2022.

PCT/US2021/064174 filed Dec. 17, 2021 International Search Report and Written Opinion dated May 18, 2022.

PCT/US2021/064642 filed Dec. 21, 2021 International Search Report and Written Opinion dated May 11, 2022.

PCT/US2021/064671 filed Dec. 21, 2021 International Search Report and Written Opinion dated May 27, 2022.

PCT/US2022/024085 filed Apr. 8, 2022 International Search Report and Wirtten Opinion dated Sep. 12, 2022.

U.S. Appl. No. 16/398,020, filed Apr. 29, 2019 Examiner's Answer dated Oct. 31, 2022.

U.S. Appl. No. 17/031,478, filed Sep. 24, 2020 Notice of Allowance dated Sep. 16, 2022.

U.S. Appl. No. 17/156,252, filed Jan. 22, 2021 Non-Final Office Action dated Oct. 25, 2022.

U.S. Appl. No. 16/398,020, filed Apr. 29, 2019 Notice of Allowance dated May 20, 2024.

U.S. Appl. No. 17/234,611, filed Apr. 19, 2021 Non-Final Office Action dated Apr. 23, 2024.

U.S. Appl. No. 17/240,591, filed Apr. 26, 2021 Advisory Action dated Feb. 22, 2024.

U.S. Appl. No. 17/240,591, filed Apr. 26, 2021 Non-Final Office Action dated Jun. 4, 2024.

U.S. Appl. No. 17/358,504, filed Jun. 25, 2021 Final Office Action dated Mar. 13, 2024.

U.S. Appl. No. 17/360,694, filed Jun. 28, 2021 Non-Final Office Action dated Feb. 14, 2024.

U.S. Appl. No. 17/390,682, filed Jul. 30, 2021 Final Office Action dated May 6, 2024.

U.S. Appl. No. 17/390,682, filed Jul. 30, 2021 Non-Final Office Action dated Jul. 5, 2024.

U.S. Appl. No. 17/392,061, filed Aug. 2, 2021 Advisory Action dated Feb. 14, 2024.

U.S. Appl. No. 17/392,061, filed Aug. 2, 2021 Non-Final Office Action dated Apr. 23, 2024.

U.S. Appl. No. 17/513,789, filed Oct. 28, 2021 Final Office Action dated Jul. 9, 2024.

U.S. Appl. No. 17/554,978, filed Dec. 17, 2021 Non-Final Office Action dated Apr. 19, 2024.

U.S. Appl. No. 17/557,924, filed Dec. 21, 2021 Final Office Action dated Feb. 29, 2024.

PCT/US2020/052536 filed Sep. 24, 2020 International Search Report and Written Opinion dated Dec. 4, 2020.

PCT/US2021/014700 filed Jan. 22, 2021 International Search Report and Written Opinion dated Jun. 29, 2021.

PCT/US2021/028018 filed Apr. 19, 2021 International Search Report and Written Opinion dated Sep. 13, 2021.

PCT/US2021/028683 filed Apr. 22, 2021 International Search Report and Written Opinion dated Sep. 16, 2021.

PCT/US2021/029183 filed Apr. 26, 2021 International Search Report and Written Opinion dated Sep. 24, 2021.

PCT/US2021/033443 filed May 20, 2021 International Search Report and Written Opinion dated Sep. 23, 2021.

PCT/US2021/039084 filed Jun. 25, 2021 International Search Report and Written Opinion dated Jan. 10, 2022.

PCT/US2021/044029 filed Jul. 30, 2021 International Search Report and Written Opinion dated Dec. 9, 2021.

(56) References Cited

OTHER PUBLICATIONS

PCT/US2021/044223 filed Aug. 2, 2021 International Search Report and Written Opinion dated Dec. 21, 2021.
PCT/US2021/048275 filed Aug. 30, 2021 International Search Report and Written Opinion dated Jan. 4, 2022.
U.S. Appl. No. 15/008,628, filed Jan. 28, 2016 Final Office Action dated May 30, 2018.
U.S. Appl. No. 15/008,628, filed Jan. 28, 2016 Non-Final Office Action dated Jan. 25, 2019.
U.S. Appl. No. 15/008,628, filed Jan. 28, 2016 Non-Final Office Action dated Nov. 2, 2017.
U.S. Appl. No. 15/008,628, filed Jan. 28, 2016 Notice of Allowance dated May 15, 2019.
U.S. Appl. No. 16/398,020, filed Apr. 29, 2019 Final Office Action dated Jan. 25, 2022.
U.S. Appl. No. 16/398,020, filed Apr. 29, 2019 Non-Final Office Action dated May 11, 2021.
U.S. Appl. No. 17/031,478, filed Sep. 24, 2020 Non-Final Office Action dated May 11, 2022.
PCT/US2022/039614 filed Aug. 5, 2022 International Search Report and Written Opinion dated Dec. 22, 2022.
PCT/US2022/044848 filed Sep. 27, 2022 International Search Report and Written Opinion dated Feb. 3, 2023.
PCT/US2022/044879 filed Sep. 27, 2022 International Search Report and Written Opinion dated Mar. 3, 2023.
PCT/US2022/044901 filed Sep. 27, 2022 International Search Report and Written Opinion dated Mar. 3, 2023.
PCT/US2022/044918 filed Sep. 27, 2022 International Search Report and Written Opinion dated Feb. 21, 2023.
PCT/US2022/044923 filed Sep. 27, 2022 International Search Report and Written Opinion dated Feb. 15, 2023.
U.S. Appl. No. 17/156,252, filed Jan. 22, 2021 Notice of Allowance dated Apr. 24, 2023.
U.S. Appl. No. 17/237,909, filed Apr. 22, 2021 Restriction Requirement dated Feb. 1, 2023.
U.S. Appl. No. 17/326,017, filed May 20, 2021 Non-Final Office Action dated Jan. 26, 2023.
U.S. Appl. No. 17/390,682, filed Jul. 30, 2021 Non-Final Office Action dated Mar. 2, 2023.
U.S. Appl. No. 17/392,061, filed Aug. 2, 2021 Restriction Requirement dated Mar. 30, 2023.
U.S. Appl. No. 17/234,611, filed Apr. 19, 2021 Final Office Action dated Sep. 20, 2024.
U.S. Appl. No. 17/240,591, filed Apr. 26, 2021 Final Office Action dated Aug. 14, 2024.
U.S. Appl. No. 17/358,504, filed Jun. 25, 2021 Notice of Allowance dated Jul. 17, 2024.
U.S. Appl. No. 17/461,619, filed Aug. 30, 2021 Restriction Requirement dated Dec. 6, 2024.
U.S. Appl. No. 17/554,978, filed Dec. 17, 2021 Notice of Allowance dated Jul. 24, 2024.
U.S. Appl. No. 17/557,924, filed Dec. 21, 2021 Non-Final Office Action dated Aug. 20, 2024.
U.S. Appl. No. 17/360,694, filed Jun. 28, 2021 Notice of Allowance dated Dec. 16, 2024.
U.S. Appl. No. 17/390,682, filed Jul. 30, 2021 Final Office Action dated Feb. 28, 2025.
U.S. Appl. No. 17/392,061, filed Aug. 2, 2021 Final Office Action dated Jan. 2, 2025.
U.S. Appl. No. 17/461,619, filed Aug. 30, 2021 Non-Final Office Action dated Feb. 11, 2025.
U.S. Appl. No. 17/513,789, filed Oct. 28, 2021 Notice of Allowance dated Jan. 3, 2025.
U.S. Appl. No. 17/557,924, filed Dec. 21, 2021 Notice of Allowance dated Dec. 11, 2024.
U.S. Appl. No. 17/234,611, filed Apr. 19, 2021 Examiner's Answer dated May 1, 2025.
U.S. Appl. No. 17/392,061, filed Aug. 2, 2021 Advisory Action dated Mar. 12, 2025.
U.S. Appl. No. 17/392,061, filed Aug. 2, 2021 Non-Final Office Action dated Apr. 5, 2025.

\* cited by examiner

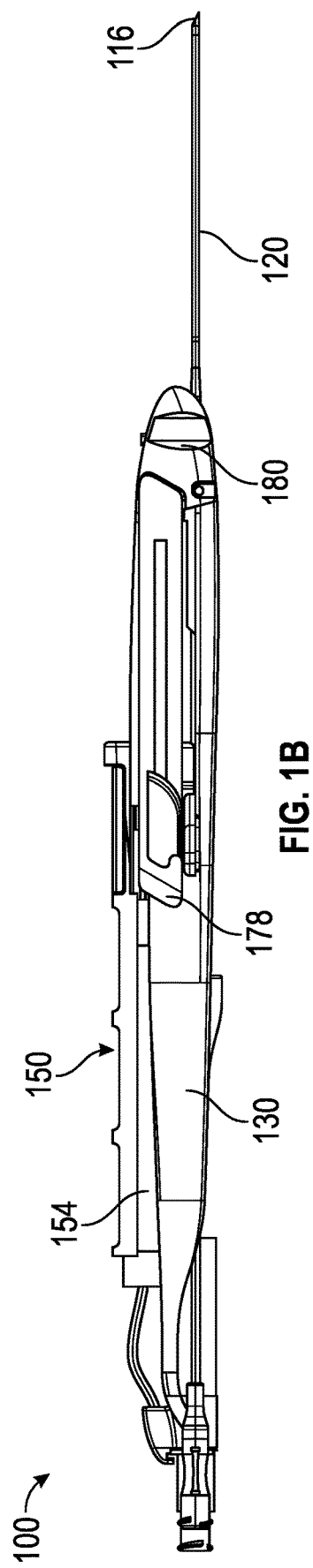
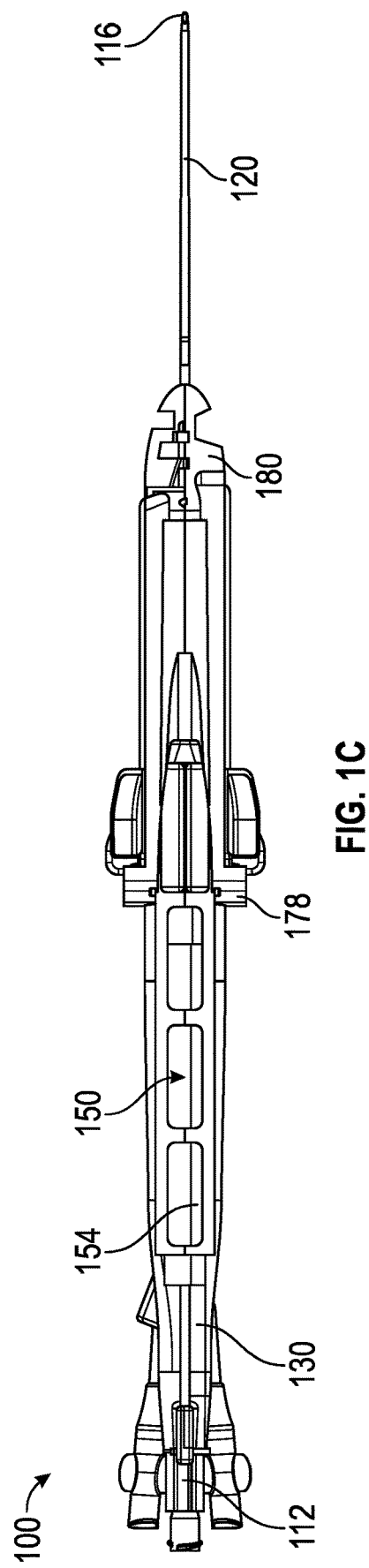
FIG. 1B
FIG. 1C

OPTIMIZED STRUCTURAL SUPPORT IN CATHETER INSERTION SYSTEMS

PRIORITY

This application claims the benefit of priority to U.S. Provisional Application No. 63/128,694, filed Dec. 21, 2020, which is incorporated by reference in its entirety into this application.

SUMMARY

Briefly summarized, embodiments disclosed herein are directed to optimized structural support devices for catheter insertion systems, and associated methods thereof. Conventional methods of placing elongate catheters, such as central venous catheters (CVC), rapid insertion central catheters (RICC), or the like, require repeated insertion and removal of multiple devices from the insertion site, and direct handling of the placement tools, catheters, devices etc. that enter the patient. Direct handling of these devices during insertion is often required to prevent buckling or kinking when an axial force is applied.

Advanced catheter insertion systems have been developed that include housings, needles, guidewires, dilators, and/or blood flash indicators configured to access the vasculature, confirm correct vascular access, dilate the insertion site and place the catheter. Advantageously, such advanced catheter insertion systems can contain the aforementioned structures within an enclosed environment to enable a "touch-free" placement of the catheter and mitigate the introduction of pathogens. Nonetheless, these insertion systems can still leave a portion of the catheter unsupported during placement, exposing the catheter to buckling or kinking when urged axially into the insertion site.

Further, when accessing the vasculature to place the catheter, a longer needle length is desirable to accommodate a broader patient base. The longer needle length can access deeper veins or penetrate deeper surface tissues. However, longer needles provide longer bending arms, i.e. a length of unsupported needle. A shorter needle bending arm, i.e. a shorter unsupported needle length, is preferable since this provides less flexion, increased accuracy, and increased tactile feedback to the clinician when accessing the vasculature. Since these advanced catheter insertion systems are provided with a needle "pre-loaded," needle exchange is not feasible and either an entirely different system must be provided to suit different patients, e.g. pediatric or adult, or a clinician must support the needle by manipulating needle itself as it enters the body, risking infection. Embodiments disclosed herein are directed to catheter placement systems with increased structural support devices to resolve the aforementioned problems.

Disclosed herein is a catheter placement system including, a needle supported by a needle hub, a catheter defining a catheter lumen, the needle extending through a portion of the catheter lumen, and a housing including, a body, a catheter advancement assembly releasably engaged with a hub of the catheter, the catheter advancement assembly slidably engaged with the body between a proximal position, a medial position, and a distal position, and a distal support slidably engaged with the body between a retracted position and an extended position, the distal support including a nose portion defining a channel to receive a portion of the catheter therethrough.

In some embodiments, the distal support is configured to transition the catheter assembly from the proximal position to the medial position as the distal support is transitioned from the retracted position to the extended position. In some embodiments, the catheter advancement assembly is configured to transition the distal support from the retracted position to the extended position as the catheter advancement assembly is transitioned from the medial position to the distal position. In some embodiments, the catheter advancement assembly includes an abutment and the body includes a cam surface, the abutment configured to engage the cam surface to urge a first portion of the body laterally apart from a second portion of the body, as the catheter advancement assembly is transitioned from the medial position to the distal position.

In some embodiments, the nose portion includes a door hingedly engaged therewith, and rotatable to an open position to allow egress of the portion of the catheter from the channel. The distal support is configured to extend distally from the housing to maintain the nose portion within a predetermined distance from a tip of the needle. The predetermined distance is a needle bending arm length of 7 cm or less. In some embodiments, the catheter placement system further includes a blood flash indicator configured to receive a blood flow from the needle lumen. In some embodiments, the catheter is a CVC catheter or a RICC catheter.

Also disclosed is a method of placing a catheter within a vasculature of a patient including, accessing the vasculature with a needle, the needle extending from a housing and including a portion of the catheter disposed annularly thereon, sliding a catheter advancement assembly from a proximal position to a medial position to advance a portion of the catheter into the vasculature, actuating a distal support from a retracted position to an extended position, advancing the catheter advancement assembly from the medial position to a distal position, separating a first portion of the housing laterally apart from a second portion of the housing, and disengaging the housing transversely upward from the catheter.

In some embodiments, the catheter advancement assembly includes an abutment configured to engage a cam surface of the housing body to separate the first portion of the housing laterally apart from the second portion of the housing, as the catheter advancement assembly transitions from the medial position to the distal position. In some embodiments, the distal support includes a nose portion defining a channel and is slidably engaged with the catheter, the nose portion providing rigid columnar support to a portion of the catheter as the catheter advancement assembly transitions from the medial position to the distal position. In some embodiments, the nose portion includes a door hingedly coupled thereto and configured to transition from a closed position to an open position to allow egress of the catheter from the channel along an axis perpendicular to a longitudinal axis.

In some embodiments, the method further includes withdrawing a needle proximally, prior to advancing the catheter advancement assembly from the proximal position. In some embodiments, the catheter advancement assembly releasably engages a portion of the catheter in an interference fit, press-fit, or snap-fit engagement. In some embodiments, the method further includes extending the distal support distally from the housing to maintain the nose portion within a predetermined distance from a tip of the needle. In some embodiments, the predetermined distance is a needle bending arm length of 7 cm or less. In some embodiments, the method further includes sliding a blood flash indicator along a longitudinal axis to create a vacuum and draw a blood flow through a lumen of the needle. In some embodiments, the catheter is a CVC catheter or a RICC catheter.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 1B shows a side view of an exemplary catheter insertion system, in accordance with embodiments disclosed herein.

FIG. 1C shows a plan view of an exemplary catheter insertion system, in accordance with embodiments disclosed herein.

DESCRIPTION

Figure 1A:
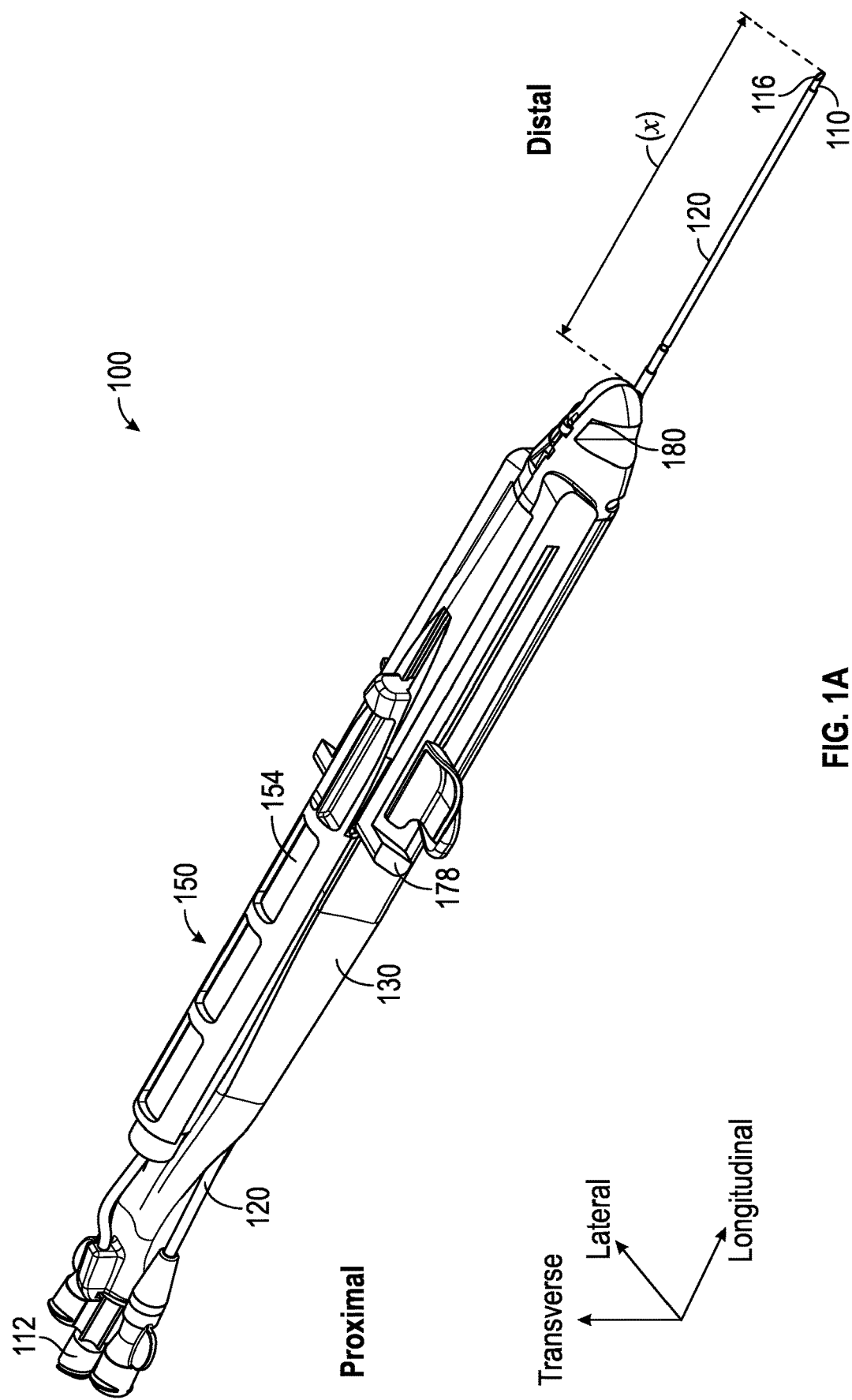
FIG. 1A shows a perspective view of an exemplary catheter insertion system, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

In the following description, the terms "or" and "and/or" as used herein are to be interpreted as inclusive or meaning any one or any combination. As an example, "A, B or C" or "A, B and/or C" mean "any of the following, A, B, C, A and B, A and C, B and C, A, B and C." An exception to this definition will occur only when a combination of elements, components, functions, steps or acts are in some way inherently mutually exclusive.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

To assist in the description of embodiments described herein, as shown in FIG. 1A, a longitudinal axis extends substantially parallel to an axial length of the catheter. A lateral axis extends normal to the longitudinal axis, and a transverse axis extends normal to both the longitudinal and lateral axes. A horizontal plane can be defined by the longitudinal and lateral axes, a vertical plane can extend perpendicular to the horizontal plane. Unless defined otherwise, all technical and scientific terms used herein have the same meaning as commonly understood by those of ordinary skill in the art.

FIGS. 1A-2A show an exemplary catheter insertion system ("system") 100, generally including a needle 110, a catheter 120, a housing 130, and a blood flash indicator 150. Optionally, the insertion system 100 can further include one or more guidewires (not shown). The needle 110 can define a needle lumen 114 and is supported by a needle hub 112 disposed at a proximal end thereof. The needle 110 can be configured to extend through at least a portion of a lumen of the catheter 120. A distal tip 116 of the needle 110 can extend distally of the distal tip of the catheter 120 and can define a sharpened tip configured for skin puncture and vascular access.

Figure 2A:
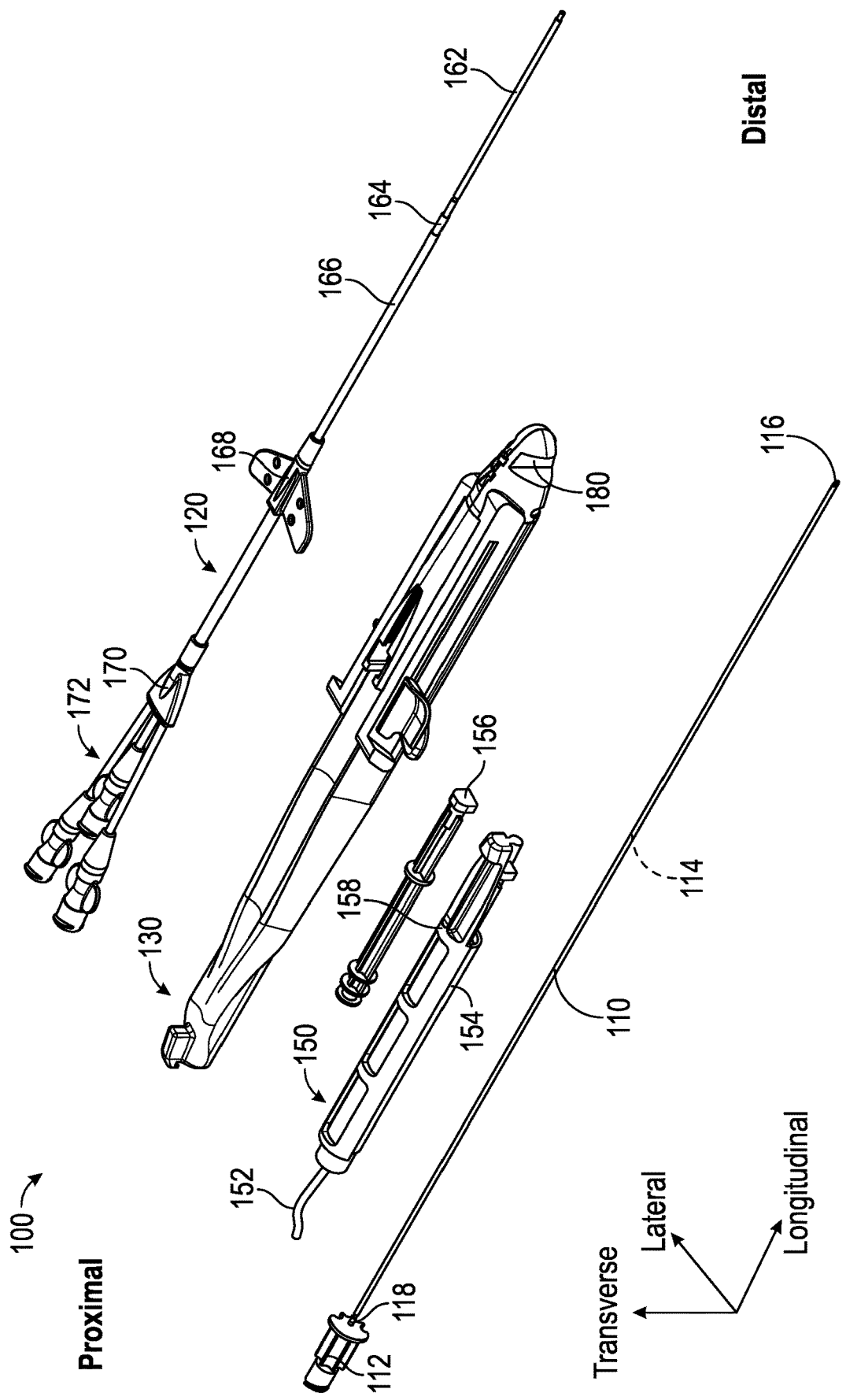
FIG. 2A shows an exploded view of an exemplary catheter insertion system, in accordance with embodiments disclosed herein.

The catheter 120 can be a central venous catheter (CVC), a rapid insertion central catheter (RICC), or similar elongate catheter configured to provide access to a vasculature of a patient. As shown in FIG. 2A, the catheter 120 can be a RICC catheter 120 including an access section 162 defining a first diameter, a dilation section 164, and a catheter body section 166 defining a second diameter, larger than the first diameter.

The access section 162 can define a single lumen and can be formed of a harder durometer material relative to the catheter body section 166. The catheter body section 166 can define one or more lumen and can be formed of a softer, more compliant material relative to the access section 162. The dilation section 164 can be formed of either the same material as the access section 162, or of a third material. The third material can be of a harder durometer relative to the material of the catheter body section 166. The dilation section 164 can provide a tapered transition between the first diameter of the access section 162 and the second diameter of the catheter body section 166. The access section 162 and the dilation section 164 can provide relatively more rigid mechanical properties and can be relatively more resistant to kinking or collapsing when an axial force is applied thereto, relative to the catheter body section 166. The catheter body section 166 can be relatively more compliant to facilitate negotiating tortuous vascular pathways. In an embodiment, the catheter 120 can further include a hub 168, a bifurcation 170, and/or one or more extension 172 legs each communicating with a lumen of the catheter 120. In an embodiment, the needle 110 can extend through an extension leg 172, through a lumen of the catheter body section 166 and through a lumen of the access section 162 to extend distally of a distal tip of the catheter 120.

The catheter insertion system 100 can further include a housing 130 configured to support the needle 110 and the catheter 120, as described in more detail herein. The catheter insertion system 100 can further include a blood flash indicator 150 in fluid communication with the needle lumen 114. The blood flash indicator 150 can include a container configured to receive a blood flow therein. The container can be formed of a transparent material to allow a user to observe a color and pulsatile flow disposed therein. In an embodiment, the blood flash indicator can include a vacutainer configured to maintain a vacuum therein to facilitate drawing a blood flow proximally through the needle lumen 114 and into the vacutainer.

In an embodiment, the blood flash indicator 150 can include a syringe barrel 154 and a plunger 156, slidably engaged therewith and configured to create a vacuum to draw a blood flow proximally through the needle lumen 114 and into the syringe barrel 154. In an embodiment, the plunger 156 can be fixedly engaged with the housing 130 to prevent any longitudinal movement relative thereto. The plunger 156 can be engaged with the housing 130 with an interference fit, snap-fit, press-fit engagement, adhesive, weld, bonding, or the like. The syringe barrel 154 can be supported by a barrel cradle 158. The barrel 154 and barrel cradle 158 assembly can be slidable relative to the plunger 156 and housing 130 assembly, and configured such that sliding the barrel 154 and cradle 158 assembly proximally can create a vacuum within the barrel 154. In an embodiment, the barrel cradle 158 can be formed of a transparent material.

In an embodiment, the blood flash indicator 150 can be fluidly coupled with the needle lumen 114 by way of a flexible tube 152, or the like. Advantageously, the flexible tube 152 can allow the syringe barrel to slide proximally relative to the needle interface 140. Advantageously, by reversing the operation of the syringe blood flash indicator 150, the syringe barrel 154 can be slid proximally to create the vacuum and reduce a length of the fluid path between the blood flash indicator 150 and the needle tip 116. Further, the action of the syringe barrel 154 and plunger 156 still allows a clinician to leverage the tactile and visual feedback offered via syringe-based blood flashback systems. Advantageously, moving the syringe barrel 154 proximally moves the barrel 154 away from the distal end of the insertion device 100 providing a clearer line of sight at the insertion site and allows for operations to occur, for example the manipulation of guidewire advancement assemblies, catheter advancement assemblies, hinging housing portions, or the like.

In use, a clinician can access a vasculature by inserting a needle tip 116 and a distal portion of the access section 162 into the vasculature. A blood flow can flow proximally through the needle lumen 114 to a blood flash indicator 150. A color and pulsatile flow can be observed to confirm correct vascular access. In case of incorrect vascular access, the access section 162 can be withdrawn and the insertion site closed by applying pressure, due to the relatively small diameter of the access section 162. Where correct vascular access is confirmed, the catheter 120 can be advanced, optionally over a guidewire, until a dilation section 164 enters the insertion site and dilates the insertion site to the second diameter of the catheter body section 166. The catheter body section 166 can then be advanced until a distal portion of the catheter is at a target location within the vasculature. Further details of RICC catheters and associated insertion systems and methods can be found in U.S. Pat. No. 10,376,675; U.S. Patent Publications U.S. 2019/0255294, U.S. 2021/0069471, U.S. 2021/0085927, U.S. 2021/0113809, U.S. 2021/0113810, U.S. 2021/0121661, U.S. 2021/0121667, U.S. 2021/0228843, U.S. 2021/0322729, U.S. 2021/0330941, U.S. 2021/0330942, and U.S. 2021/0361915, each of which are incorporated by reference in its entirety into this application.

Figure 2B:
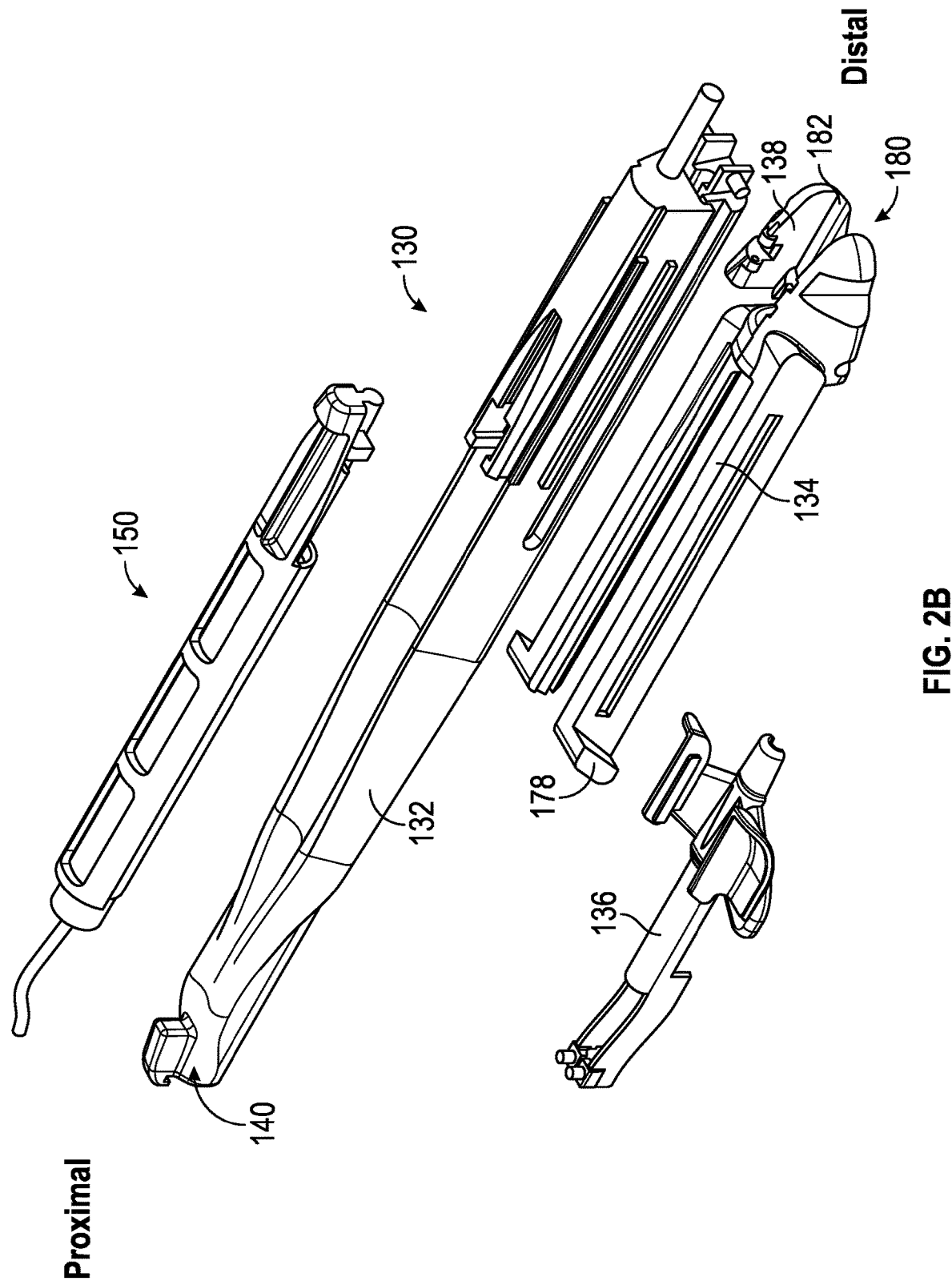
FIG. 2B shows an exploded view of a housing of an exemplary catheter insertion system, in accordance with embodiments disclosed herein.

FIG. 2B shows further details of the housing 130 generally including a body 132, a distal support 134, a catheter advancement assembly 136 and a blood flash indicator 150. The housing 130 can include a body 132 including a needle interface 140 disposed at a proximal end and configured to provide fluid communication between the needle lumen 114 and the blood flash indicator 150 by way of an aperture 118 disposed in a wall of the needle 110. A distal support 134 can be slidably engaged with the body 132 along a longitudinal axis between a retracted position (FIG. 3D) and an extended position (FIG. 3E). The distal support 134 can include a handle 178 configured to allow a user to grasp the distal support 134 and transition the distal support 134 between the retracted position and the extended position.

The distal support 134 can further include a nose portion 180 disposed at a distal end and defining a channel 182 extending along the longitudinal axis and configured to receive a portion of the catheter 120 therethrough. The catheter 120 can be slidably engaged with the channel 182. As such, the distal support 134 can engage the catheter 120 and provide a rigid, columnar support to the catheter 120 to prevent buckling or kinking of the catheter 120 when a longitudinal axial force is applied. Further, as described in more detail herein, the distal support 134 can extend distally to support a portion of the catheter 120 that has been advanced from the housing 130. This can provide columnar support to the catheter 120 while preventing a user from having to touch portions of the catheter 120 that are intended to enter the body of the patient.

In like manner, the distal support 134 can also provide rigid support to a portion of the needle 110. As described herein, while a longer needle can be advantageous to accommodate a broader patient base, access deeper veins, or penetrate deeper surface tissues, a shorter bending arm (x)

(FIG. 1A) is preferred to provide improved accuracy, and improved tactile feedback. Typically a bending arm (x) length of 7 cm or less is preferred however, greater or lesser lengths are also contemplated depending on the material or structure of the needle 110. As such, where a needle tip 116 is extended from the housing 130 beyond the predetermined bending arm length (x), a user can extend the distal support 134 to provide a ridged support to the needle 110 within the predetermined bending arm length (x) from the needle tip 116.

In an embodiment, the nose portion 180 can include one or more doors 138 hingedly coupled with the distal support 134. In an embodiment, as shown in FIG. 3I, the door(s) 138 can rotate through an arc extending through a vertical plane, perpendicular to the longitudinal axis between a closed position and an open position. In an embodiment, as shown in FIG. 3H, the door(s) 138 can rotate laterally through an arc extending through a horizontal plane, between a closed position and an open position. In the closed position, the door 138 can prevent egress of the portion of catheter 120 from the channel 182. In the opening position, the door 138 can allow ingress or egress of the portion of catheter 120 to/from the channel 182.

In an embodiment, the catheter advancement assembly 136 can be slidably engaged with the body 132 along the longitudinal axis between a proximal position (FIG. 3C), a medial position (FIG. 3D), and a distal position (FIG. 3E). The catheter advancement assembly 136 can releasably engage a portion of the catheter 120. For example, the catheter advancement assembly 136 can releasably retain the catheter hub 168 in an interference fit, press-fit, or snap-fit engagement. However it will be appreciated that other mechanisms to releasably engage the catheter 120 are also contemplated. Further, it will be appreciated that the catheter advancement assembly 136 can engage other portions of the catheter 120, for example, the catheter body section 166, the bifurcation 170, combinations thereof, or the like. Sliding the catheter advancement assembly 136 between the proximal position, medial position, and distal position can advance the catheter 120 along a longitudinal axis.

Figure 3A:
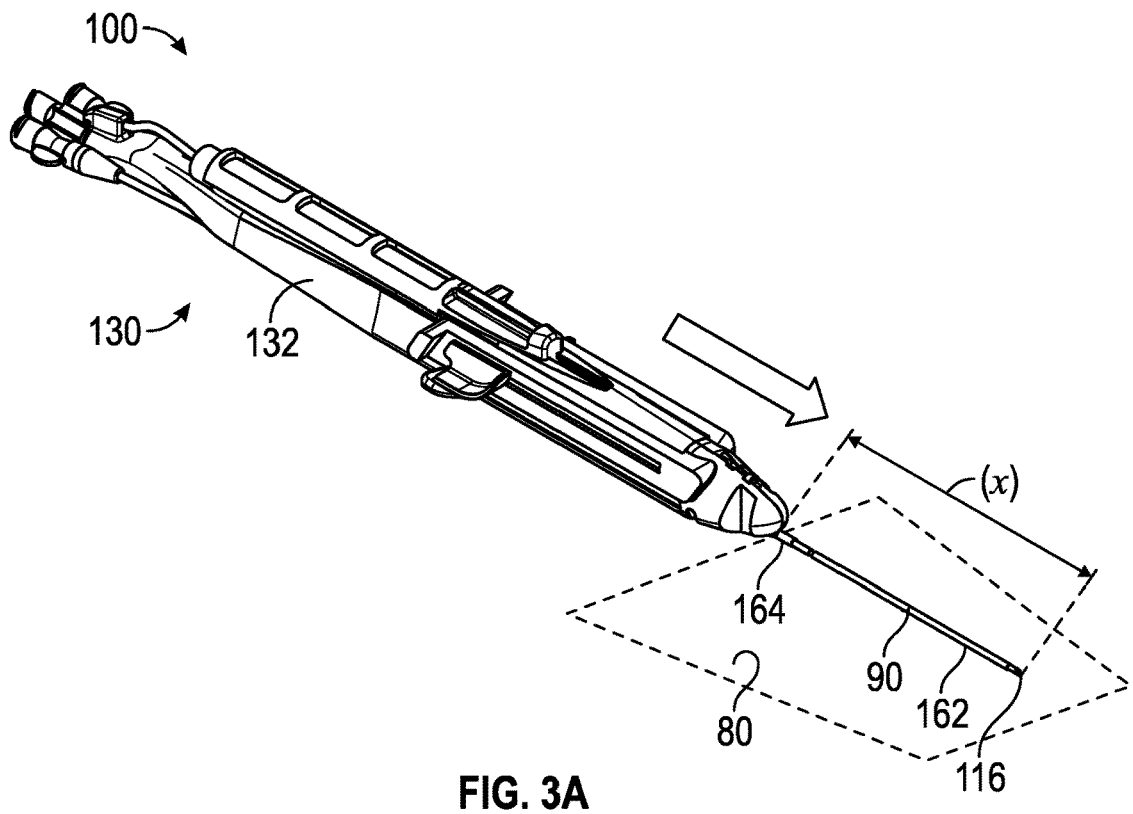
FIGS. 3A-3J show an exemplary method of use for a catheter insertion system, in accordance with embodiments disclosed herein.
Figure 3B:
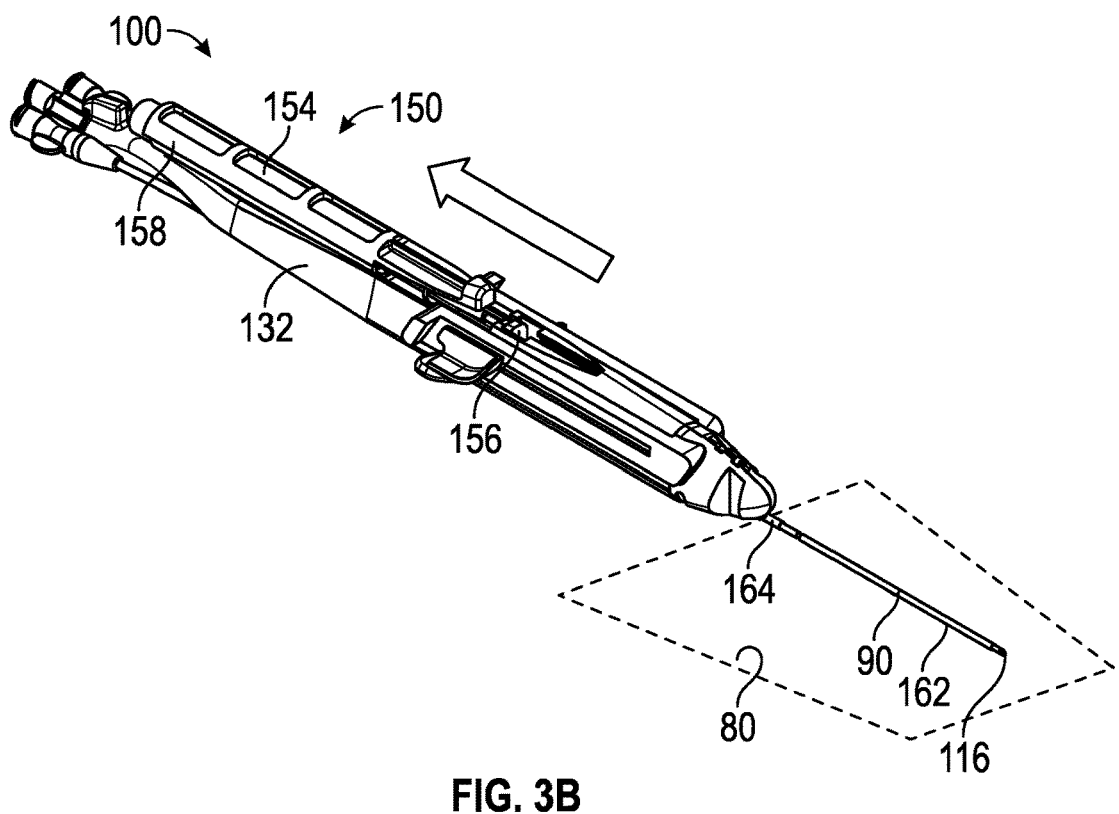
Figure 3C:
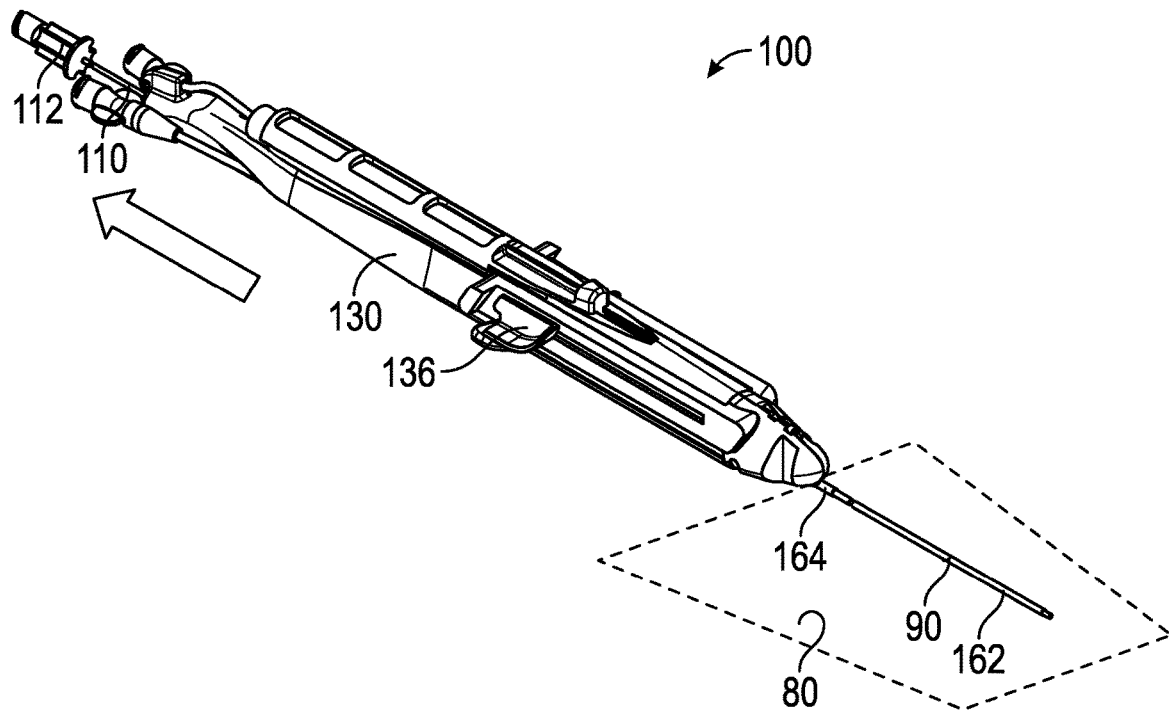
Figure 3D:
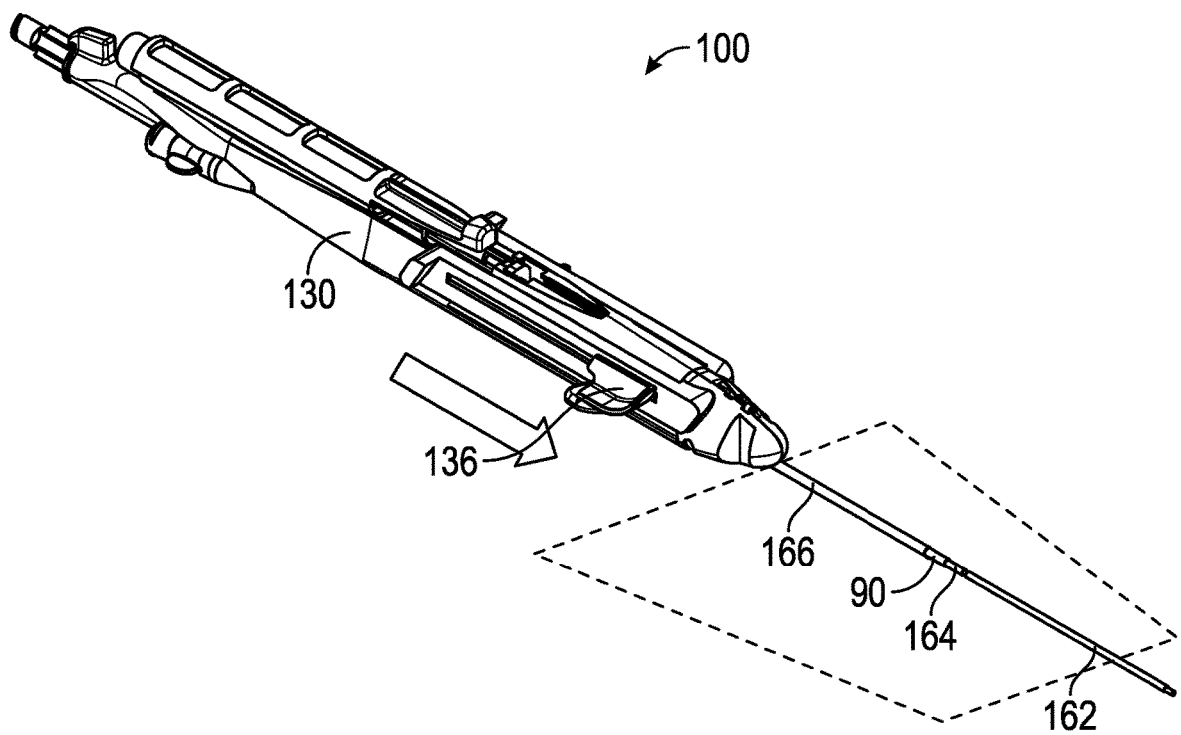
Figure 3E:
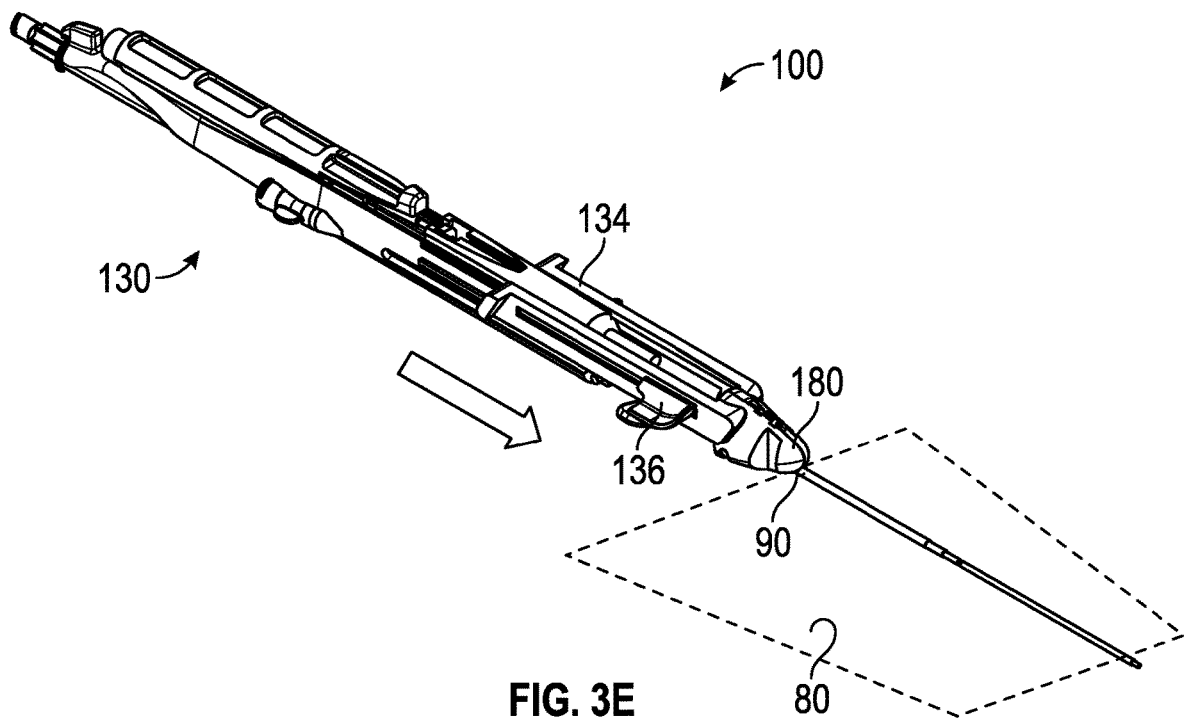
Figure 3F:
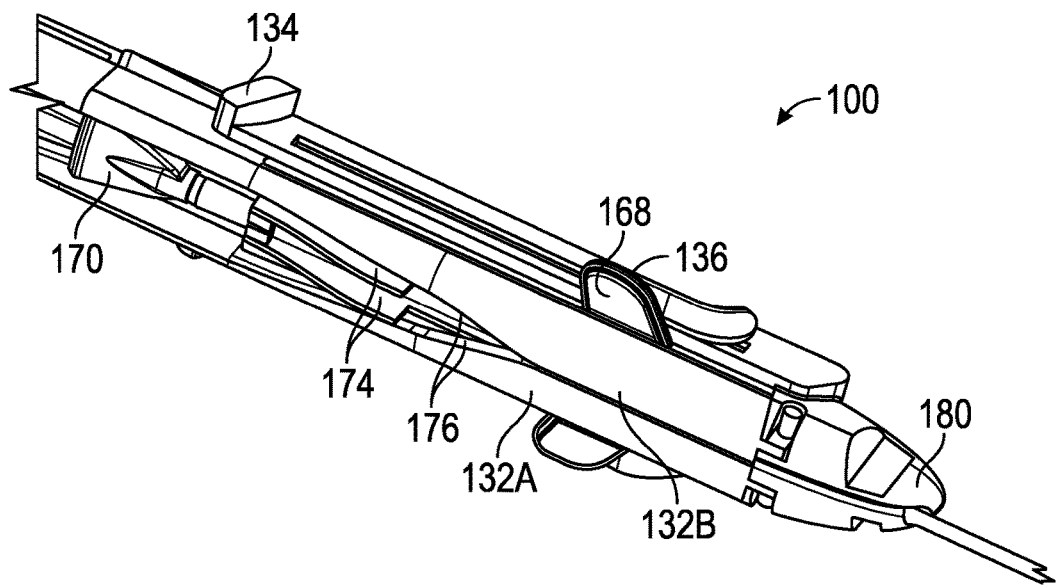
Figure 3G:
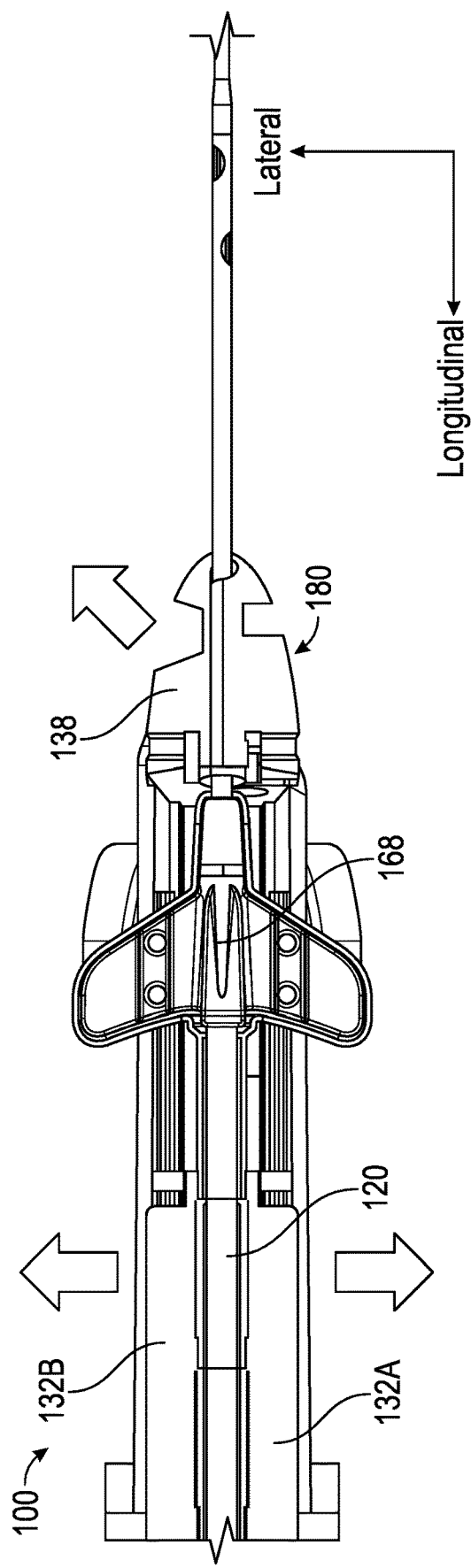
Figure 3I:
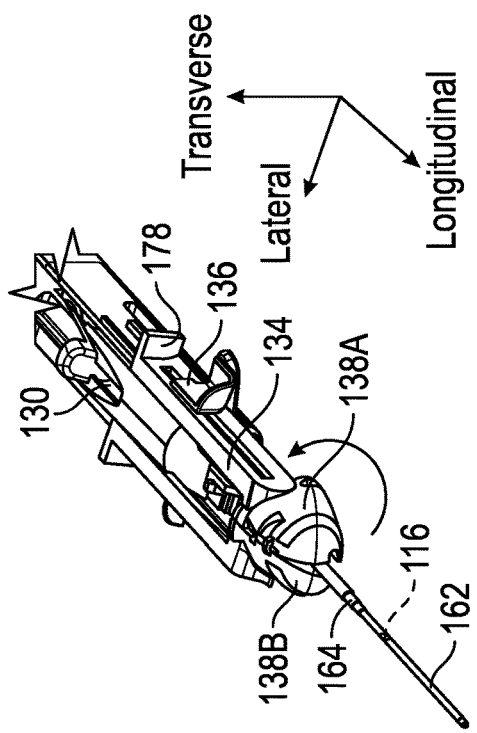
Figure 3H:
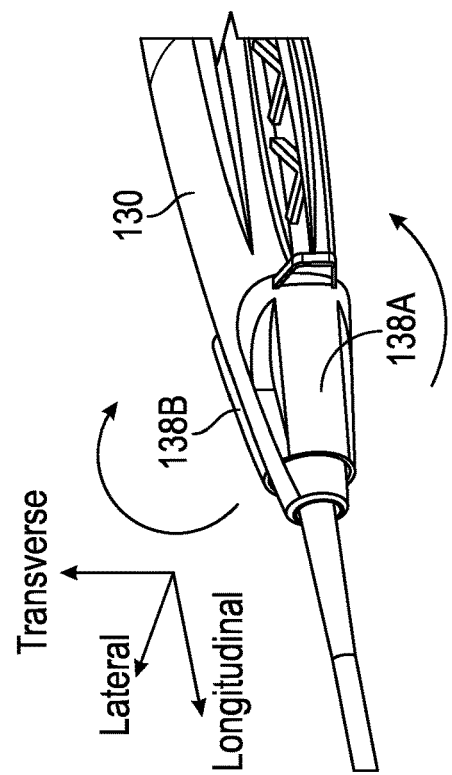

FIGS. 3A-3J show an exemplary method of use for the catheter insertion system 100. As shown in FIG. 3A, a user can grasp the housing 130 and advance a needle tip 116 through a skin surface 80 of the patient to create an insertion site 90 and access a vasculature of the patient therebelow. As described herein, the needle tip 116 can extend from the housing 130 by a predetermined distance (x). The predetermined distance (x), i.e., needle bending arm, will be within a tolerance to provide support to the needle 110, but to prevent bending or breaking of the needle 110 when a force is applied. In an embodiment, the predetermined distance (x) is equal to or less then 7 cm, however, greater or lesser values are also contemplated. As will be appreciated, the predetermined distance (x) can vary depending on the structure and material of the needle 110.

As shown in FIG. 3B, a user can actuate a barrel cradle 158 to slide the syringe barrel 154 in a proximal direction relative to the housing body 132. The plunger 156, being coupled to the housing body 132, remains stationary relative to the housing 130, as the barrel 154 slides proximally, creating a vacuum within the syringe barrel 154. The vacuum draws a blood flow proximally through the needle lumen 114, through the needle aperture 118, through the needle interface 140, through the flexible tube 152 and into the syringe barrel 154. As noted herein, the syringe barrel 154 and optionally the barrel cradle 158 can be formed of a transparent material to facilitate observation of the blood flow color and pulsatile flow.

As shown in FIG. 3C, once vascular access has been confirmed, the needle hub 112 can be withdrawn proximally to withdraw the tip 116 proximally of the distal tip of the catheter 120. In an embodiment, the needle 110 can be withdrawn further, for example, so that the needle tip 116 is proximal of one of the access section 162, dilation section 164, the catheter body section 166, the hub 168, the bifurcation 170, or withdrawn from the catheter 120 entirely.

As shown in FIG. 3D, a user can then slide the catheter advancement assembly 136 and the catheter 120, coupled thereto, from the proximal position to the medial position to advance the catheter 120 into the insertion site 90. As the dilation section 164 is urged into the insertion site 90, the insertion site 90 is dilated to the second diameter of the catheter body section 166. To note, the catheter body section 166 can include two or more lumen that each communicate with an opening disposed in a side wall of the catheter body section 166 adjacent the dilation section 164.

When the catheter advancement assembly 136 is advanced to the medial position (FIG. 3D) the distal support 134 can slide distally from the housing body 132 (FIG. 3E) from the retracted position to the extended position. In an embodiment, the catheter advancement assembly 136 can be advanced to the medial position simultaneously with the distal support 134 being advanced to the extended position. Advantageously, the simultaneous advancement of the catheter advancement assembly 136 and the distal support 134 allows the nose portion 180 to provide rigid support to the catheter 120 as the catheter 120 is advanced. In an embodiment, with the distal support 134 in the extended position, the catheter advancement assembly 136 can advance from the medial position (FIG. 3D) to the distal position (FIG. 3E). Advantageously, the catheter advancement assembly 136 and the distal support 134 can be selectively advanced by the user to advance the catheter 120 and provide support to the catheter 120 to prevent buckling or kinking of the catheter 120 without having to directly touch portions of the catheter 120 that are to enter the patient's body.

In an embodiment, the system 100 can include one or more gears, levers, or similar mechanisms to provide mechanical advantage between the longitudinal movement of one or both of the distal support 134 and the catheter advancement assembly 136 and the resulting movement of one or both of the nose portion 180 and the catheter 120. For example, as shown in FIGS. 3C-3E, a 1:1 mechanical advantage is shown where for a single unit of longitudinal distance of user input, a single unit of longitudinal distance of output is achieved, i.e. 1 cm of distal support handle 178 movement results in 1 cm of nose portion 180 movement. Similarly, 1 cm of catheter advancement assembly 136 movement results in 1 cm of catheter 120 movement. In an embodiment, the system 100 can include mechanisms to provide a 1:>1 mechanical advantage, i.e. 1 cm of distal support handle 178 movement results in >1 cm of nose portion 180 movement. Similarly, 1 cm of catheter advancement assembly 136 movement results in >1 cm of catheter 120 movement.

FIGS. 3F-3G show close up detail of an underside view of the system 100. In an embodiment, as shown in FIGS. 3F-3G, the catheter advancement assembly 136 can include an abutment surface 174 configured to engage a cam surface 176 of the housing body 132. As the catheter advancement assembly 136 transitions from the medial position (FIG. 3F) to the distal position, the abutment surface 174 can engage the cam surface 176 to urge two or more portions 132A, 132B of the housing body 132 laterally apart. Separating the housing portions 132A, 132B can provide a longitudinal opening to allow the housing body 132 to disengage the catheter 120 in a transverse direction, as described in more detail herein. FIG. 3G shows an underside view of the system 100 with the catheter advancement assembly 136 in the distal position and the distal support 134 in the extended position.

Figure 3J:
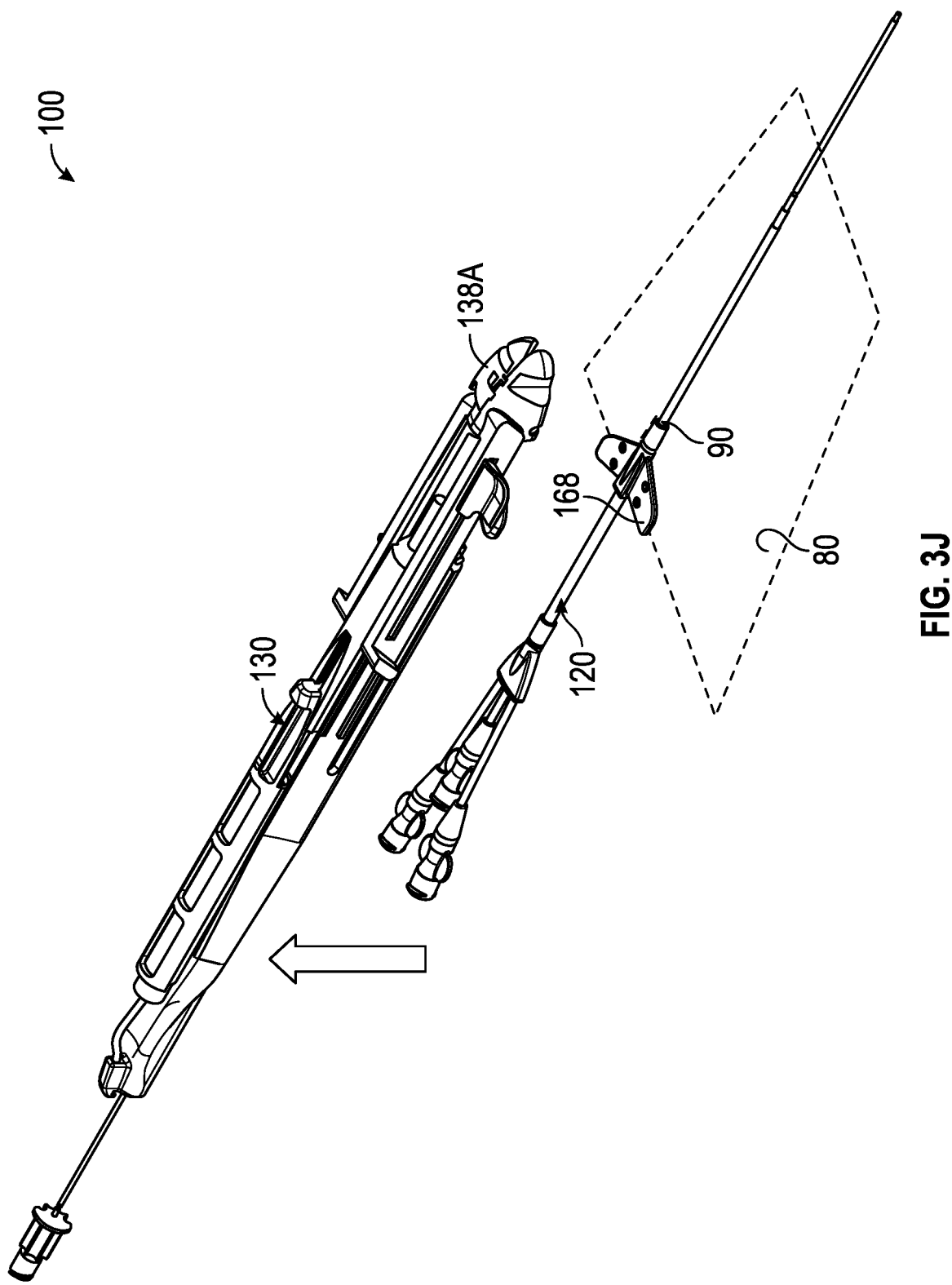

As shown in FIGS. 3H-3J, with the distal support 134 in the extended position and the catheter advancement assembly 136 in the distal position, the catheter 120 is placed within the vasculature with the catheter hub 168 is disposed adjacent the insertion site 90. Advantageously, the user can place the catheter 120 as such without having to directly touch the catheter 120 distally of the catheter hub 168. Once the catheter 120 is placed, the door 138 of the nose piece 180 can rotate to an open position to allow the nose piece 180 to disengage the catheter 120 (FIGS. 3H, 3I). In an embodiment, as shown in FIG. 3H, the system 100 can include a first door 138A and a second door 138, each configured to rotate relative to the housing 130. In an embodiment, the door(s) 138 through a longitudinal axis, either through a vertical plane, a horizontal plane, or at an angle relative thereto. In an embodiment, as shown in FIG. 3I, a first door 138A can rotate relative to a second door 138B, the second door 138B remaining stationary relative to the housing 130. In an embodiment, the door 138 can rotate through an axis extending perpendicular to the longitudinal axis, e.g. a lateral vertical plane. These and other number, orientation, or configuration of doors 138 are contemplated to fall within the scope of the present invention. As shown in FIG. 3J, the housing 130 can then disengage the catheter 120 transversely upward, leaving the catheter 120 placed within the vasculature of the patient. Advantageously, the catheter placement system 100 can place the catheter 120 while maintaining axial support to prevent buckling and can prevent the user from touching any portion of the catheter.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A catheter placement system, comprising:
    a needle supported by a needle hub;
    a catheter defining a catheter lumen, the needle extending through a portion of the catheter lumen; and
    a housing comprising:
        a body extending between a proximal end and a distal end and configured to enclose a first portion of the catheter about a longitudinal axis;
        a catheter advancement assembly releasably engaged with a hub of the catheter, the catheter advancement assembly slidably engaged with the body between a proximal position, a medial position, and a distal position; and
        a distal support slidably engaged with a distal portion of the body between a retracted position and an extended position, the distal support including a nose portion disposed at a distal end of the distal support and defining a channel to receive a second portion of the catheter therethrough, the nose portion in the retracted position disposed distally of the distal end of the body.

2. The catheter placement system according to claim 1, wherein the distal support is configured to transition the catheter advancement assembly from the proximal position to the medial position as the distal support is transitioned from the retracted position to the extended position.

3. The catheter placement system according to claim 1, wherein the catheter advancement assembly is configured to transition the distal support from the retracted position to the extended position as the catheter advancement assembly is transitioned from the medial position to the distal position.

4. The catheter placement system according to claim 1, wherein the catheter advancement assembly includes an abutment and the body includes a cam surface, the abutment configured to engage the cam surface to urge a first portion of the body laterally apart from a second portion of the body, as the catheter advancement assembly is transitioned from the medial position to the distal position.

5. The catheter placement system according to claim 1, wherein the nose portion includes a door hingedly engaged therewith, and rotatable to an open position to allow egress of the portion of the catheter from the channel.

6. The catheter placement system according to claim 1, wherein the distal support is configured to extend distally from the housing to maintain the nose portion within a predetermined distance from a tip of the needle.

7. The catheter placement system according to claim 6, wherein the predetermined distance is a needle bending arm length of 7 cm or less.

8. The catheter placement system according to claim 1, further including a blood flash indicator configured to receive a blood flow from a lumen of the needle.

9. The catheter placement system according to claim 1, wherein the catheter is a CVC catheter or a RICC catheter.

10. A method of placing a catheter within a vasculature of a patient, comprising:
    accessing the vasculature with a needle, the needle extending from a housing and including a first portion of the catheter disposed annularly thereon, the housing including a body extending between a proximal end and a distal end and configured to enclose a second portion of the catheter about a longitudinal axis;
    sliding a catheter advancement assembly from a proximal position to a medial position to advance the first portion of the catheter into the vasculature;
    actuating a distal support from a retracted position to an extended position, the distal support slidably engaged with the body and having a nose portion disposed distally of the body in both the retracted position and the extended position;
    advancing the catheter advancement assembly from the medial position to a distal position;
    separating a first portion of the housing laterally apart from a second portion of the housing; and
    disengaging the housing transversely upward from the catheter.

11. The method according to claim 10, wherein the catheter advancement assembly includes an abutment configured to engage a cam surface of the body of the housing to separate the first portion of the housing laterally apart from the second portion of the housing, as the catheter advancement assembly transitions from the medial position to the distal position.

12. The method according to claim 10, wherein the nose portion defines a channel and is slidably engaged with the catheter, the nose portion providing rigid columnar support to a portion of the catheter as the catheter advancement assembly transitions from the medial position to the distal position.

13. The method according to claim 12, wherein the nose portion includes a door hingedly coupled thereto and configured to transition from a closed position to an open position to allow egress of the catheter from the channel along an axis perpendicular to the longitudinal axis.

14. The method according to claim 10, further comprising withdrawing the needle proximally, prior to advancing the catheter advancement assembly from the proximal position.

15. The method according to claim 10, wherein the catheter advancement assembly releasably engages a portion of the catheter in an interference fit, press-fit, or snap-fit engagement.

16. The method according to claim 12, further comprising extending the distal support distally from the housing to maintain the nose portion within a predetermined distance from a tip of the needle.

17. The method according to claim 16, wherein the predetermined distance is a needle bending arm length of 7 cm or less.

18. The method according to claim 10, further comprising sliding a blood flash indicator along the longitudinal axis to create a vacuum and draw a blood flow through a lumen of the needle.

19. The method according to claim 10, wherein the catheter is a CVC catheter or a RICC catheter.

* * * * *